(12) United States Patent
Scoley et al.

(10) Patent No.: US 12,384,541 B2
(45) Date of Patent: Aug. 12, 2025

(54) VEHICLE LAVATORY SINK BASIN ASSEMBLY

(71) Applicant: Safran Cabin Inc., Huntington Beach, CA (US)

(72) Inventors: Ian Scoley, Huntington Beach, CA (US); Mike Romero, Huntington Beach, CA (US); Eric Heimbach, Huntington Beach, CA (US)

(73) Assignee: Safran Cabin Inc., Huntington Beach, CA (US)

( * ) Notice: Subject to any disclaimer, the term of this patent is extended or adjusted under 35 U.S.C. 154(b) by 75 days.

(21) Appl. No.: 18/272,199

(22) PCT Filed: Jan. 19, 2021

(86) PCT No.: PCT/US2021/013860
§ 371 (c)(1),
(2) Date: Jul. 13, 2023

(87) PCT Pub. No.: WO2022/159070
PCT Pub. Date: Jul. 28, 2022

(65) Prior Publication Data
US 2024/0300649 A1 Sep. 12, 2024

(51) Int. Cl.
*B64D 11/02* (2006.01)
*A61L 2/10* (2006.01)
(Continued)

(52) U.S. Cl.
CPC ............... *B64D 11/02* (2013.01); *A61L 2/10* (2013.01); *A61L 2/26* (2013.01); *B60R 15/04* (2013.01);
(Continued)

(58) Field of Classification Search
CPC ... B64D 11/02; A61L 2/10; A61L 2/26; A61L 2202/11; A61L 2202/25; B60R 15/04; E03D 9/002; B61D 35/005
See application file for complete search history.

(56) References Cited

U.S. PATENT DOCUMENTS

| 4,884,767 A | 12/1989 | Shibata |
| 2005/0230539 A1 | 10/2005 | Quan |

(Continued)

FOREIGN PATENT DOCUMENTS

| CN | 102428002 A | 4/2012 |
| EP | 1683456 B1 | 9/2008 |

(Continued)

OTHER PUBLICATIONS

European Application No. 21921541.5, Extended European Search Report mailed on Aug. 7, 2024, 10 pages.

(Continued)

*Primary Examiner* — Christine J Skubinna
(74) *Attorney, Agent, or Firm* — Kilpatrick Townsend & Stockton LLP

(57) ABSTRACT

A vehicle lavatory monument assembly that includes an enclosure having first, second, third and fourth walls that cooperate to define a lavatory interior, an entry door positioned on the second wall, and a sink basin assembly positioned in the lavatory interior. The sink basin assembly includes a sink basin that includes a back wall, a top wall, a bottom wall, a first side wall, and a second side wall that cooperate to defined a sink basin interior. The top wall includes a top surface and a bottom surface, the bottom surface partially defines the sink basin interior, and the top surface is a counter.

11 Claims, 16 Drawing Sheets

(51) Int. Cl.
 A61L 2/26 (2006.01)
 B60R 15/04 (2006.01)
(52) U.S. Cl.
 CPC ........ *A61L 2202/11* (2013.01); *A61L 2202/25* (2013.01)

(56) References Cited

U.S. PATENT DOCUMENTS

| | | |
|---|---|---|
| 2006/0289698 A1 | 12/2006 | Quan |
| 2013/0082140 A1 | 4/2013 | Ehlers et al. |
| 2015/0282682 A1 | 10/2015 | Bayley et al. |
| 2018/0064833 A1 | 3/2018 | Childress et al. |
| 2018/0112382 A1 | 4/2018 | Voetter |
| 2018/0265202 A1 | 9/2018 | Koyama et al. |
| 2020/0130843 A1 | 4/2020 | Young |
| 2020/0180767 A1 | 6/2020 | Koyama |
| 2020/0247544 A1 | 8/2020 | Pothier |

FOREIGN PATENT DOCUMENTS

| | | |
|---|---|---|
| EP | 2907753 A1 | 8/2015 |
| EP | 2939923 A1 | 11/2015 |
| EP | 3002217 B1 | 8/2018 |
| JP | 1150198 A | 2/1999 |
| JP | 2016074412 A | 8/2015 |
| JP | 2018069028 A | 6/2017 |
| JP | 2019024528 A | 7/2017 |
| WO | 2019194215 A1 | 10/2019 |

OTHER PUBLICATIONS

International Patent Application No. PCT/US2021/013860, International Search Report and Written Opinion, dated Apr. 26, 2021.
Japanese Application No. 2023-543275, Office Action mailed on Aug. 23, 2024, 11 pages (4 pages of Original Document and 7 pages of English Translation).
Japanese Application No. 2023-543275, Office Action mailed on Mar. 7, 2025, 7 pages (3 pages of Original Document and 4 pages of English Translation).

VEHICLE LAVATORY SINK BASIN ASSEMBLY

FIELD OF THE INVENTION

The present invention relates generally to a clean lavatory for an aircraft or other vehicle.

BACKGROUND OF THE INVENTION

Commercial airline operations have been disrupted by the Covid 19 crisis. As a result, there is a desire to develop and deploy technology, products, and solutions that clean, sanitize, disinfect, or even sterilize the aircraft interior before, during or after flight. As used herein, "cleaning" means clean, sanitize, sterilize, replenish or any combination thereof.

Aircraft flying in commercial service must be fuel efficient and safe to fly. The airframe manufacturers, suppliers, and government regulators, such as the FAA, have developed procedures, regulations, processes and requirements to ensure products that are introduced into the aircraft are safe, meet requirements and regulations, are low weight, lower power, and compact in volume.

Although solutions for cleaning aircraft interiors have been proposed to airline operators, there is still a need to ensure these technologies, products, or solutions also meet the industry needs of efficiency and safety at the same time. Moreover, commercial products are being adapted for use on aircraft, but these products may not meet the industry requirements to allow them to fly or to be certified as airborne equipment.

The air in the cabin of an aircraft is typically recirculated approximately twenty times every hour. In addition, the fresh air that enters the cabin is filtered. This provides a cabin atmosphere that is cleaner than many other forms of public transportation. However, the lavatory is one area of the cabin where a passenger is confined to a small space where the air is not recirculated as often as in the open cabin. This can increase the chances that airborne pathogens spread during air travel. In an attempt to reduce the spread of such pathogens, the air inside of a lavatory can be recirculated every time a passenger uses the lavatory.

The killing of bacteria and viruses by ultraviolet (UV) light or sanitization occurs on surfaces that are in a direct "line of sight" of the light rays emitted by the UV light source. Optimal sanitization occurs when the angle of incidence is 0°, in other words, when the light ray is perpendicular or normal as it leaves the lamp and strikes the surface. The sanitization effectiveness is decreased if the UV rays are at an angle relative to the surface that needs to be sanitized. The effectiveness of the UV light decreases as the angle of incidence increases. For reference, the sanitization intensity is reduced by approximately 10% at a 20° angle of incidence and approximately 40% at a 30° angle. In addition, the farther away the UV light source is from the surface that is to be sanitized, the lower the intensity of the light on the sanitization surface. This decreases sanitization effectiveness. For reference, the intensity of a UV-C light is reduced approximately 95% at a distance of approximately one meter from the light source.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

The present invention is directed to a clean lavatory that includes one or more features. Generally, the clean lavatory addresses passenger hygiene concerns by providing integrated touchless solutions (such as water and soap/sanitizer dispensing) and eliminating airborne contaminates on demand (e.g., using an air replenishment system), mitigating crew cleaning and replenishing challenges by implementing surface geometry that is easy to clean and consolidating consumables (such as wipes) into one or very few stowage areas that are easily accessible from the cabin aisle (or otherwise outside the lavatory enclosure) even when the lavatory is occupied, and providing methods to communicate lavatory sanitary status to passengers without the need of crew involvement.

In accordance with an aspect of the present invention, there is provided a vehicle lavatory monument assembly that includes an enclosure with a plurality of walls that cooperate to define a lavatory interior with an entry door is positioned on one of the plurality of walls and a tower assembly positioned on and extends outwardly from one of the plurality of walls. A sanitizing recess is defined in a front surface of the tower assembly, and the sanitizing recess includes access to hand sanitizer therein. The hand sanitizer may be associated with a liquid or gel dispenser, a sanitizing wipe or the like.

In a preferred embodiment, the present invention provides a station or tower assembly that is stocked with and includes a hand sanitizer dispenser and/or sanitizing wipes that are accessible directly from the aircraft cabin aisle using a tower assembly that has one or more access doors therein. The tower assembly preferably provides a hygiene station to passengers that is accessible from the aisle (i.e., outside the lavatory) and also provides information to passengers regarding the cleanliness of the lavatory and the steps taken to keep the lavatory and/or cabin as clean as possible.

In a preferred embodiment, the stationary tower or tower assembly is integrated into an aircraft monument such as a lavatory or a galley or is located next to a monument such as a lavatory or galley. The tower includes but is not limited to a touchless hand sanitizer dispenser, a sanitizing wipe dispenser, and/or a receptacle for trash. The trash receptacle is located inside of a trash compartment or trash receptacle space on the inside of the tower and/or in the lavatory interior. The hand sanitizer dispenser and/or sanitizing wipe dispenser are both accessible from the aircraft cabin aisle. The trash compartment is accessible from either within the lavatory, or from the aisle via the trash receptacle in the tower. The trash container is emptied from the aisle-side of the tower, which reduces the need for crew or maintenance personnel to enter the lavatory for maintenance.

In a preferred embodiment, an access panel or door located in the upper side of the tower provides access to the disposable tissue and towel dispensers (all towels, tissues, wipes, etc. may be referred to herein as wipes) that are located and accessible within the lavatory. This reduces the need for crew or maintenance personnel to enter the lavatory for maintenance and to replace the wipes.

In a preferred embodiment, a display panel is located on the outside of the tower. This display panel uses illuminated information or graphics, display screens, or integrated color-coded wash-lights to convey status information to crew and/or passengers. This information can include but is not limited to service information such as the approximate time that beverage carts will be coming through the cabin, cleaning status such as the cleaning methods and cleaning protocols used in the lavatory, how long since the air in the lavatory was replenished and lavatory availability/vacancy. The display screen can include illuminated icons that activate to communicate vacant, occupied, cleaning, in service, etc. or the display screen can be an embedded flat screen display to run information graphics like on-board hygiene procedures and technologies or include advertising.

It will be appreciated that passengers have access to a hygiene station that does not require entering a lavatory because the sanitizing items can be accessed from the aisle. In addition, the display screen provides passengers with additional information related to the procedures and technologies that are being used to increase the cleanliness within the cabin which aides in increasing passenger confidence in flight travel.

In accordance with an aspect of the present invention, there is provided a vehicle lavatory monument assembly that includes an enclosure that includes a plurality of walls that cooperate to define a lavatory interior with an entry door and an inlet, a toilet that includes an outlet positioned in the lavatory interior, and an air replenishment system configured to move a first volume of air from the lavatory interior and through the outlet and a second volume of air through the inlet an into the lavatory interior.

In a preferred embodiment, the present invention also provides the ability to remove airborne pathogens after each use of the lavatory. The present invention provides the ability to generate air flow, using existing or newly created air inlets and the toilet as an outlet. Air inlets may be active (forced air from ECS system) or passive (ventilation openings to the general cabin). The location of the inlet(s) can be customized compared to the prior art. In a preferred embodiment, the toilet dry flush cycle is used to suck or pull the air out of the lavatory, providing airborne pathogen elimination and air circulation. The dry flush cycle is used without passenger presence and can be customized in flow and duration. Therefore, the lavatory vacuum system can be repurposed or used to remove the air from the lavatory after every lavatory use. This provides a fresh air environment for every passenger that uses the lavatory. In a preferred embodiment, the air recirculation or replenishment system inside the aircraft lavatory has a cycle time under 30 seconds and can communicate the current air quality inside of the lavatory to passengers or crew.

In a preferred embodiment, the toilet vacuum system (or a separate vacuum system) is used in dry mode (without water) to suck air from the lavatory interior. The toilet flush valve (or outlet) opening time is electronically programmed based on the required volume of air to be extracted and the location of the one or more inlets. A toilet dry flush is a short time, high volume operation generating flow around 150 l/s, for example. This vacuum system can be activated automatically after a passenger exits the lavatory, or manually by pressing a button (or otherwise activating a switch) that is located outside of the lavatory. Manual activation of the vacuum system is disabled when a person is inside of the lavatory. In a preferred embodiment, the vacuum takes approximately ten seconds to remove the volume of air that is inside of the lavatory. It will be appreciated that the volume of air that is moved out of the lavatory is at least the majority of the air in the lavatory. Some air may be extracted from or moved out the outlet of the toilet during regular flushing (the outlet in a typical aircraft toilet is open for about four seconds during a normal flush, which may result in some air escaping through the outlet). However, this is not sufficient to clean or replenish the air in the lavatory. Therefore, for purposes of the present invention, the first volume of air that is moved out of the lavatory is at least half of the volume of the air present in the lavatory interior prior to activation of the air replenishment system, and as much as 100% of the air. The typical aircraft lavatory volume is around 1.1 m$^3$. Air flow through the toilet at 0° and 1 atm is approximately 0.117 m$^3$/sec. Therefore, it should take approximately 10 seconds to completely remove the full volume of lavatory air (a first volume of air). This period of time may be longer for a lavatory with a larger volume or shorter for a lavatory with a smaller volume. Due to the pressure differential between the inside and the outside of the lavatory, cabin air enters the lavatory through the lavatory door decompression vents and/or ECS inlets (which may be located, e.g., behind the mirror). In an embodiment, a HEPA (or other air filter) is located within the decompression vent to filter the air entering the lavatory. An air fragrance cartridge or dispenser can also be located within the decompression vent to introduce a fresh scent to the air entering the lavatory. In another embodiment, the air fragrance cartridge or dispenser can be located in another area of the lavatory such as above the ceiling panel.

In the preferred embodiment, an indicator on the outside of the lavatory communicates the air quality level within the lavatory. This indicator or display screen or member can include information including but not limited to: the amount of time passed since the last air recirculation cycle, an indication of color such as red to show that the air was not recirculated after the last passenger used the lavatory or green to show that the air has been recirculated after the last passenger has used the lavatory, and/or an indication of the lavatory status such as "vacant" or "occupied,"

In accordance with an aspect of the present invention, there is provided a vehicle lavatory monument assembly that includes an enclosure having a plurality of walls that cooperate to define a lavatory interior, an entry door positioned on one of the plurality of walls, and a UV sanitization system that includes a first light module positioned in the lavatory interior. The first light module includes an ultraviolet light source that emits ultraviolet light rays and a lens member. The UV sanitization system includes a first reflective surface that includes a reflective coating thereon, a first direct surface to be sanitized, and a first indirect surface to be sanitized. The lens member is configured to direct ultraviolet light rays to the first direct surface to be sanitized. The lens member is also configured to direct ultraviolet light rays to the first reflective surface and the first reflective surface is angled to direct ultraviolet light rays to the first indirect surface to be sanitized. If indirect surface to be sanitized is flat, preferably, the ultraviolet light rays that reflect off the first reflective surface reach the first indirect surface to be sanitized at an angle between 30° and 90°, more preferably, the angle is between 60° and 90° and most preferably, the angle is between 75° and 90°. These same angle ranges apply to the light rays directed to the direct surface to be sanitized.

In a preferred embodiment, the UV sanitization system includes a controller that is configured to activate the UV sanitization system a predetermined number of seconds after the lavatory interior has been vacated. In a preferred embodiment, the UV sanitization system includes a controller that is configured to activate the UV sanitization system a predetermined amount of time after a previous activation of the UV sanitization system. In another embodiment, the UV sanitization system or at least certain lights therein can be activated while a person is in the lavatory. For example, while a person is using the toilet, the sink can be UV sanitized. Sensors can be provided for determining the location of the passenger in the lavatory and for determining which light modules within the system can be activated.

In a preferred embodiment, the first reflective surface is located adjacent to a non-reflective surface. In some embodiments, the first reflective surface is not parallel to the non-reflective surface. In a preferred embodiment, the lens member includes a first portion with a first thickness and a second portion with a second thickness. The first portion is configured to direct ultraviolet light rays to the first direct surface to be sanitized and the second portion is configured to direct ultraviolet light rays to the first reflective surface (the light rays may be directed at a different angles to the direct and indirect surfaces to be sanitized).

In a preferred embodiment, the UV sanitization system includes a manual activation switch configured to activate the UV sanitization system that is located outside the lavatory interior (e.g., on the outside of the entry door). Preferably, the manual activation switch is part of an activation assembly that includes an indication system that is configured to indicate a UV sanitization status of the lavatory interior. In a preferred embodiment, the indication system includes a plurality of indication lights that include a first indication state and a second indication state. The first indication state indicates that the vehicle interior is clean and the second indication state indicates that the vehicle interior is not clean. In a preferred embodiment, the manual activation switch is disabled when the lavatory interior is occupied and/or the manual activation switch is disabled when the entry door is locked.

In a preferred embodiment, the present invention includes UV sanitization system for providing UV light sanitizing on at least some of the surfaces in the aircraft interior and/or the lavatory interior. For example, the UV light may be FUV (222 nm wavelength), UV-C, UV-B, etc. It will be appreciated that the areas of the lavatory that have the highest number of touchpoints are the door handles, the areas around the sink and countertop including the faucets, soap dispensers, and waste flaps, and also certain areas associated with the toilet bowl and toilet shroud, such as the flush button, seat cover dispenser, seat and cover. Areas with higher number of touchpoints increase the probability of the spreading of pathogens in those areas and therefore require more focus for sanitization to reduce the risk of spreading pathogens. Therefore, the application of UV light to these high touchpoint surfaces can help sanitize the surfaces and reduce the risk of transmission of viruses and the like.

Furthermore, surface films or coatings applied to surfaces within the lavatory are able to reflect approximately 95% of the UV light that hits the coated surfaces. Therefore, one solution is to position a UV lamp or light source such that the rays are directed perpendicular to and as close to the high risk surfaces as possible. However, this may not be feasible due to multiple reasons including cost and power considerations. Therefore, the present invention positions a UV lamp as close to the high risk surfaces as feasibly possible, modifying the effectivity angle with the geometry of the UV lamp lens (e.g., refracting the rays), and uses UV reflective surfaces to direct the UV light to the high risk surfaces as efficiently as possible to maximize the sanitization potential. Generally, the present invention provides a sanitization system that quickly kills pathogens on high risk surfaces in a lavatory in a way that ensures that the desired surfaces are sanitized after each passenger use.

In a preferred embodiment, for sanitizing the sink and countertop area, a UV light source is located under the mirror of the lavatory. This UV light source contains a lens that can direct the UV light as desired to specific surfaces to be sanitized. To redirect or angle the light, the lens can include portions of variable thickness. The lens cover directs the UV light waves or rays (e.g., via refraction) in a specified direction and angle, sometimes referred to herein as "the effectivity angle." At least some of the surfaces of the lavatory sink and countertop are coated in UV reflective materials. Therefore, when UV light hits these surfaces, a portion of the UV light is reflected at an angle normal to the UV reflection surface, referred to herein as "the reflection angle." The UV reflection may be done using mirrors. The effectivity angle and reflection angles of the system are configured in a way such that the UV light from the UV light source hits specific targets in the lavatory.

These targets include but are not limited to: the countertop surface, specifically around the sink perimeter and waste flap perimeter, the surfaces of the waste flap, the surfaces within the sink bowl, the surfaces of the sink faucets and handles; including the undersides of the faucets and handles, the surfaces of the soap dispenser, including the underside of the soap dispenser, the surfaces surrounding the paper towel/wipe/tissue dispenser(s), and the surfaces of the interior door handle, including the underside of the door handle.

In a preferred embodiment, one or more UV light sources can be located under the baby change table, on one or more of the walls of the lavatory underneath a shroud or cover, underneath the seat cover dispenser and/or under the toilet shroud of the lavatory. The UV light source contains a lens covering of variable thickness that directs the UV light waves in a specified direction and angle, the effectivity angle. The surfaces around the toilet seat of the lavatory are coated in UV reflective materials. These surfaces can include but are not limited to: the walls surrounding the toilet seat, the lavatory floor pan, the toilet shroud, and/or the toilet bowl. When UV light hits these surfaces, a portion of the UV light is reflected at an angle normal to the UV reflection surface, which may be referred to herein as the reflection angle. The effectivity angle and reflection angles of the system are configured in a way such that the UV light from the UV light source hits specific targets in the lavatory. In order to ensure that the target surface is hit by the UV light, the geometry of the toilet can be modified, or shrouds, reflective surfaces, panels or the like can be added to the lavatory walls or other components and coated with UV reflective materials to provide the needed reflection angle.

Other targets can include but are not limited to: the surface of the toilet flush button, the surfaces surrounding the seat cover dispenser, all surfaces of the toilet paper dispenser, including the underside of the dispenser, and the surface of the toilet lid.

The present invention includes compact, wide effectivity UV lamps. As discussed above, the effectivity of these lamps is influenced by the geometry of the lens over the lamp, specifically by varying the thickness of the lens. The UV lamps are preferably located in discreet locations of the lavatory.

This invention also includes UV reflective materials that can be applied to specific reflective surfaces of the lavatory (therefore providing reflective surfaces and non-reflective surfaces that do not include coating thereon). These UV reflective surfaces direct the UV light so that it hits the surfaces of the lavatory that have a high number of passenger touchpoints, which are the surfaces most responsible for spreading pathogens between passengers. It will be appreciated that the light disinfects faster when it is closer to the surface to be sanitized (indirect or direct). The light disinfects faster when it is pointing directly at the infection (like a spotlight: move to the side and the illumination disappears quickly). The longer the light illuminates a surface, the more energy is absorbed by the microbe and the more complete the disinfection. Approximately 1 minute of UV light on a surface that is approximately 20″ from the light source provides greater than 99.9% disinfection. Approximately 10 minutes of UV light on a surface that is approximately 20″ from the light source provides greater than 99.999% disinfection.

This combination of wide effectivity UV lamps and UV reflective surfaces creates a UV sanitizing solution that maximizes surface cleaning rate and effectiveness in an automated manner. One key enabler in the present invention is a UV lamp form factor that fits underneath a lavatory mirror and/or other discreet locations and a variable thickness light lens that provides a focused effectivity angle. A second key enabler is the application of UV reflective materials to lavatory surfaces, which allows UV light to be directed to targets that are typically not within line-of-sight of the UV light source, such as underneath faucet handles or door knobs. Combining the two enablers described above creates an automated UV sanitization system that enables cleaning effectiveness. This is achieved by locating the UV light source close to the target cleaning surfaces and orienting the UV light through light reflection so that the direction of the light wave is as close as possible to the normal of the target cleaning surface. These factors increase the amount of energy that is transferred into sanitizing and affecting pathogens on the target surface. This reduces the amount of time that the target surface needs to be exposed to the UV light to be sanitized.

The present invention also allows the sanitization process to be automated so that maintenance crews do not need to use UV wands or apply sanitizing chemicals for the target surfaces to be sanitized. For example, the UV sanitization system can be activated at predetermined times or after each use of the lavatory (similar to the air replenishment system discussed herein). In a preferred embodiment, the air replenishment system and UV sanitization system are both activated after each use of the lavatory. In a preferred embodiment, the UV sanitization system can be activated using the manual activation button/switch described herein. It will be appreciated that the automated UV sanitization system and process can be tuned to a high level of performance or sanitization, where manual maintenance items like wands and sprays are dependent on staff training and discipline and may have much more variable results with less effectiveness than assumed. Preferably, the UV sanitization system is configured to not be activated or to not activate the ultraviolet lights when a person is in the lavatory (e.g., when the door is locked or when a person is sensed to be in the lavatory interior). In an embodiment, the UV sanitization system may not include any indirect surfaces to be sanitized.

In a preferred embodiment, the aircraft lavatory monument assembly also provides for optimization of the cleanliness of aircraft lavatories by reducing the factors that typically lead to uncleanliness such as split lines between adjacent parts, horizontal surfaces near the sinks that allow water to pool, and the presence of objects that extend vertically from horizontal surfaces such as soap dispensers and water faucets that make cleaning around these objects difficult.

In accordance with an aspect of the present invention, there is provided a vehicle lavatory monument assembly that includes an enclosure having first, second, third and fourth walls that cooperate to define a lavatory interior, an entry door is positioned on the second wall, and a sink basin assembly positioned in the lavatory interior. The sink basin assembly includes a sink basin that includes a back wall, a top wall, a bottom wall, a first side wall, and a second side wall that cooperate to defined a sink basin interior. The top wall includes a top surface and a bottom surface and the bottom surface partially defines the sink basin interior. The top surface is a counter.

In a preferred embodiment, a sink basin that includes a mouth or opening through which a user places their hands that is oriented generally vertically replaces the traditional sink bowl that is typically oriented horizontally. The geometry of the sink basin helps prevent water from congregating on horizontal surfaces (such as the typical countertop located adjacent the sink mouth) and forces water through a drain at the bottom of the basin due to gravity. The sink basin preferably also has a smaller footprint than a traditional combined sink bowl and countertop which frees up space within the lavatory. In a preferred embodiment, the leading edge of the sink basin is shaped to provide a hand-hold for passenger stability during turbulence.

In a preferred embodiment, the embodiment, the lavatory monument assembly also includes a "dry shelf" located above the sink basin. Personal items such as cell phones or cosmetics can be placed on this dry shelf, which remains dry because all of the liquids remain contained in the sink basin below the dry shelf. In a preferred embodiment, also contained within or below the dry shelf are touchless water and soap dispensers that are within or dispense into the sink basin interior. In use, when a user inserts their hands into the sink basin and underneath the touchless water dispenser, the presence of the hands are captured by motion sensors, IR distance sensors, or other technology used to activate the touchless devices. When the water dispenser is activated, water flows from the dispenser. When a user inserts their hands into the sink basin and underneath the touchless soap dispenser, the presence of the hands are captured by motion sensors, IR distance sensors, or other technology used to activate touchless devices. When the soap dispenser is activated, soap flows from the dispenser.

In a preferred embodiment, a UV sanitization light is located within and/or below the dry shelf, and activates when hands are not present in the sink basin or when otherwise activated (e.g., by a switch, system, etc.). This UV light sanitizes the surfaces within the sink basin.

In a preferred embodiment, there are few to no visible attachment hardware on the exposed surfaces of the sink basin or dry shelf. This makes the exposed surfaces of the sink basin and dry shelf easy to clean by crew or maintenance personnel. Preferably, the sink basin or water bowl and dry shelf are removable using concealed fasteners.

In a preferred embodiment, the sink basin requires little to no hand contact with any surfaces when used, is easy to wipe clean and the components thereof are easy to remove for deep cleaning, maintenance or exchange. It will be appreciated that the enclosed nature of the design means that potentially damaging UV virus destroying technology can be focused where it is most effective and least harmful (as it can be potentially skin damaging through extended exposure). The over/under arrangement of wet and dry zones (e.g., the dry shelf over the sink basin) makes it so that furniture is less intrusive within the lavatory space, lessening the risk of passenger contact to adjacent, potentially unhygienic, surfaces.

The sink basin isolates the hand washing function of a lavatory within a clean environment and embeds typically hard to clean equipment (like the faucet and soap dispenser) within a flush, easy-wipe surface (within the dry shelf) and by allowing for the safe integration of active and passive biocidal technologies. Preferably, easy deep clean maintenance is enabled by making all major contact surfaces quickly removable without the need to uncouple system interfaces. However, this is not a limitation on the present invention.

In accordance with an aspect of the present invention, there is provided a vehicle lavatory monument assembly that includes An enclosure having a plurality of walls that cooperate to define a lavatory interior, a door is positioned on one of the plurality of walls, and a first component positioned in the lavatory interior that includes a first visual indication coating on an outer surface thereof. The first visual indication coating includes at least a first excitation additive that is configured to illuminate when irradiated by a first light that includes light waves within a predetermined wavelength range. Preferably, the predetermined wavelength range is within the ultraviolet range. The range may be the entire ultraviolet range or a subset thereof.

In accordance with another aspect of the present invention, there is provided a method of sanitizing a component that includes covering at least a portion of an outer surface of the component with a first visual indication coating. The first visual indication coating includes at least a first excitation additive that is configured to illuminate when irradiated by a first light that includes light waves within a predetermined wavelength range. The method also includes directing an ultraviolet light source toward an outer surface of the first visual indication coating to sanitize the outer surface of the first visual indication coating, such that the first excitation additive is illuminated at a first level. In a preferred embodiment, the first excitation additive is a first fluorescing additive and the method further includes moving the ultraviolet light source closer to the outer surface of the first visual indication coating, such that the first excitation additive is illuminated at a second level that is brighter than the first level.

In a preferred embodiment, the present invention includes a sanitization system that includes both active and passive sanitization methods. The passive sanitization can be done by adding antimicrobial coatings, films or the like to the surfaces within the lavatory. The active sanitization can include using a UV wand or light to sanitize surfaces. The UV sanitization can be done by a crew member in between flights or at other predetermined times. The UV sanitization can also be done automatically either at predetermined time intervals during a flight or after each use of the bathroom using the UV sanitization system described herein. The invention includes sanitizing an aircraft lavatory using anti-microbial additives in coatings or films that are applied to the surfaces that passengers tend to touch the most. In the present invention, "passive" refers to the visual indication and not the anti-microbial effect. Passive indication is the luminescing visual indicator that the part is sanitized. It is passive in that the spot absorbs UV light and as long as the energy is in the material it retains a visual indication (glowing/color light/hologram) that the part is protected. Active is the indicator that the part has a UV wand or light energy directed at the surface. The glow is only apparent with the focused light energy. Passive refers generally to where no further action from users is necessary to provide clean/sanitize/disinfection surfaces. It will be appreciated by those of ordinary skill in the art that "continuously active" is the phrase used by the Environmental Protection Agency for these types of materials, but indicating that the antimicrobial agents are always in effect beyond the initial application.

It will be appreciated that there are several mechanisms that can be used to disrupt and destroy bacteria, viruses, and fungal organisms and prevent them from propagating in an aircraft. Generally, these mechanisms for disrupting and destroying bacteria, viruses, and fungal organisms and preventing them from propagating in an aircraft are referred to herein as "sanitizing" or "cleaning."

Electro/polar attraction is the addition of conductive materials (e.g., silver and copper are common) that have an ionic charge that attracts and disrupts microbial activity. This form of passive sanitization may be referred to herein as "conductive sanitization" and the materials may be referred to herein as "conductive sanitizers." Another method includes mechanical disruption, where the surface or additive has a rough surface topography. Microbes have a difficult time anchoring to the rough or undulating surface to form a colony, and the roughness can also be so rough that it can tear or fracture cell membranes, killing bacteria, and interrupting virus proliferation. This form of passive sanitization may be referred to herein as "mechanical disruption sanitization" and the materials may be referred to herein as "mechanical disruption sanitizers."

UV radiation can also be used, as specific and particular wavelengths can focus on the cellular wall causing it to rupture and render the bacteria, germ, or virus harmless. This form of "energized" sanitization may be referred to herein as "UV sanitization" and the materials may be referred to herein as "UV sanitizers." This requires some skill or technique of the operation to insure proper sanitation occurs and that the entire surface is efficiently sanitized For the methods where sanitization is accomplished by the surface topography, chemical, electrical attraction, or mechanical means, these methods discussed herein, those of ordinary skill in the art will be able to appreciate that it is difficult to determine how effective the anti-microbial additives are at performing the task of killing microbes, and it is also difficult to determine if the anti-microbial additives are still present on the surfaces to be cleaned. For example, in the case of electrical or chemical means, the additive is distributed homogeneously through the medium to insure efficacy, without intervention or skill of the operator, but there is no visual or mechanical confirmation that the materials are active and working. In the respect of surface topography, or other mechanical means, the surface accomplishes the task without operator intervention and unless the surface is inspected on a microscopic scale, it cannot be determined that it is still effective.

The present invention includes the addition of additives or dyes in the sanitizing coatings or films that luminesce or illuminate when irradiated by light with a certain range of wavelengths. The luminescence provides a visual indication of sanitization. The additives can be fluorescence and/or phosphorescence dyes that are defined by the wavelength of UV or laser energy used to create the desired response. Both fluorescence and phosphorescence are based on the ability of a substance to absorb light and emit light of a longer wavelength and therefore lower energy. The main difference is the time in which it takes to do so. In fluorescence, the emission is basically immediate and therefore generally only visible, if the light source is continuously on (such as UV lights); while phosphorescent material can store the absorbed light energy for some time and release light later, resulting in an afterglow that persists after the light has been switched off.

In other words, fluorescing dyes provide an immediate response and fade quickly when the energy source (UV light or laser) is removed. Phosphorescent dyes provide a response for a sustained period of time, based on the amount of energy absorbed and the energy decay response desired. The illumination response may last between 5 seconds and several hours. The fluorescent and/or Phosphorescent dyes or additives may be referred to generally herein as "excitation additives."

The excitation additives bind or are bound to the antimicrobial additives in the sanitizing coatings/films. The excitation additives provide visual feedback (when they fluoresce) to indicate the presence of the anti-microbial additives to which they are bound. Several methods can be used to chemically bond the excitation additive to the various types of microbial disablers in the various sanitizers and sanitizing systems discussed above.

For adding a fluorescent or phosphorescent additive or dye to ionic or nano particle silver additives (the conductive sanitizers), a coating can be furnished on the particles to enhance their ionic state and stabilize it to provide long term protection. The chemistry of the dyes can be adjusted to bind or bond to the exterior shell of the coating, away from the silver particles, and when irradiated by UV or other light show a distinct color or watermark on the particles. This provides an ionic or nano particle silver additive for sanitizing that includes a coating with the dye bonded thereto coated on the conductive sanitizer.

Mechanical disruption sanitizers often include microspheres of ceramic or quaternary ammonium compounds are used to effect the surface. Dyes can be used to coat the ceramic without changing or disrupting the topography.

UV disinfection or sanitizing can be effective, as the dyes can provide feedback that the light is properly focused, with a visual indication to indicate the light is properly focused and surface irradiation is properly dosed. The intensity or color can be the visual indicator.

Exemplary formulations of excitation additives include SrAL204+Eu, Dy and/or Sr4a114025+Eu, Dy. Grades can be Lightnic Yellow (520 nm excitation energy) and Lightnic Blue (490 nm excitation energy). The excitation additives may not be directly bound to the antimicrobial additive, but rather dispersed through the coating or resin that includes the antimicrobial additive. One purpose of the inclusion of the excitation additives is to show that the coating is sustained or still active on the surface of the part, and not worn off the panel surface. Since the antimicrobial is also dispersed through the coating, film or resin, the excitation additive does not need to be in immediate contact with the antimicrobial.

It will be appreciated that the visual feedback provided by the excitation additives enables one or more of the following: 1) a visual indication of "high priority areas" that need longer sanitization times when using a UV wand to sanitize surfaces: 2) a visual indication that anti-microbial additives are still present and active; and 3) a visual indication that a surface has been recently sanitized with UV light. For category 2 above, the antimicrobial additives in the film may break down or not work as well over time. Thus, the excitation additive will not illuminate or may illuminate below a predetermined threshold (i.e., it is faint), thus letting the airline know that a new film needs to be applied.

The present invention provides cabin crew and/or cleaning crew with a way of visualizing the progress that has been made with respect to cleaning a surface with UV light. The spread of the light over the surface area and the application time required for the UV light to be effective in killing microbes can be better controlled if there is a way of measuring progress. Alternatively, if UV light is used as a means of disinfection within the lavatory in between passenger occupation, the change in the visual appearance of the film (e.g., coloring) can also be used as a way of indicating to a passenger that surfaces have been recently cleaned.

For example, a fluorescing dye would be used to show where the energy of the light is directed. The stronger the excitation or fluorescing response as the light is directed toward a surface, the stronger the UV light is and the better the level of sanitization is occurring. Bright or strong excitation equals strong sanitization, weak excitation equals weak sanitization. The phosphorescent dyes are preferably on a marker or conspicuous area of the component (e.g., the toilet seat) so that the technician or the passenger has a good indication that the material has been affected and sanitized.

In a first preferred embodiment, uniform UV-fluorescent additives are added to the antimicrobial coating or film. In a preferred embodiment, the UV-florescent additives bind to the antimicrobial additives through a chemical bond to the ionic or mechanically disruptive antimicrobial additives. In another preferred embodiment, When the surface is exposed to black light or UV light, the UV-fluorescent additives illuminate in a cobalt blue, green, red (or other desired) color. This indicates to the crew or maintenance personnel that the anti-microbial additives are still present and performing the purpose of eliminating pathogens. If the surface does not illuminate the predetermined color (or illuminates below a predetermined threshold), this indicates that the anti-microbial additives are no longer present (or are present below a predetermined threshold).

In another preferred embodiment, UV-fluorescent additives of a first group that have the property of illuminating a specific color when exposed to UV-light due to irradiance and half-life properties of the UV-fluorescent additives are added to specific areas of an anti-microbial film. In addition, UV-fluorescent additives of a second group that have the property of illuminating a color that is different from the first group of UV-fluorescent additives are added to different areas of the anti-microbial film than the first group of UV-fluorescent additives. In an embodiment, UV-fluorescent additives of additional groupings that have the property of illuminating colors that are different from the first or second grouping of UV-fluorescent additives can be added to areas of the anti-microbial film where the first or second groupings of UV-fluorescent additives are not present. As the surfaces that are covered by the anti-microbial film are exposed to UV-light, such as the UV-light from a UV sanitizing wand, the UV-fluorescent additives illuminate the color that is dictated by the UV-fluorescent additive properties such as irradiance and half-life. The surface that contains the first grouping of UV-fluorescent additives illuminate one color (a first color), the surface that contains the second group of UV-fluorescent additives illuminates a color that is different from the first group of UV-fluorescent additives (a second color), and if additional UV-fluorescent groupings are present in the anti-microbial film, the surface that contains additional groupings of UV-fluorescent additives illuminate colors that are different from the other groups of UV-fluorescent additives (third or more colors). The first color may indicate a high touch area that requires longer sanitization time than the area with the second color, which is a lower touch area. In use, the areas of the surface that need additional sanitization time can be visually indicated to the crew or maintenance personnel. Areas that need additional sanitization time are illuminated one color when exposed to the UV-light of a UV sanitizing wand, and areas that need less sanitization are illuminated a different color when exposed to the UV-light of a UV sanitizing wand.

In a preferred embodiment, the two technologies, phosphorescing dye and fluorescing dye, are combined. As discussed above, a UV fluorescing dye glows immediately to show a directional sanitizing UV wand or light is properly directed at the panel. The phosphorescing dye absorb light photons and stay "lit," "illuminated" or "excited" or it may glow as a marker or confidence builder for the crew or passenger that shows the surface has been recently cleaned or sanitized.

The interior lavatory toilet seat is used as an example. In use, a crew member (or the automated UV sanitization system discussed herein) broadcasts a UV light over the surface of the toilet seat and sanitizes and eliminates microbes from the surface. As UV light is invisible to the naked eye, the glowing surface treatment allows the technician (if there is a technician, or during maintenance cycles of the automated system to insure the UV lamps or directional lights are properly focused on the surface) to verify where they have applied the light and cleaned the surface. The phosphorescent dye remains illuminated for a longer period of time and allows the passenger who enters the lavatory after the treatment to see and know that the toilet seat surface has been cleaned or sanitized and is safe.

In another embodiment, additives that have UV energy absorption properties are added to the antimicrobial surfaces in a specific and/or predetermined pattern. In a preferred embodiment, the method for applying these additives in a specific pattern can be ink-jet printing. However, this is not a limitation and the pattern can be created other ways. When a surface that contains the additives is exposed to UV light, the additives are energized and emit visible light until the energy dissipates. This provides a visual indication to crew, maintenance personnel, and/or passengers when a surface has recently been cleaned using UV light. If the predetermined pattern on the surface emits light, this indicates that the surface has been recently cleaned. For example, the predetermined pattern may be a word or words, such as "SANITIZED" or may be a logo, emblem or other visual indicator.

In a preferred embodiment, the excitation additive or phosphorescent additive can be added to the coating using an inkjet printer or the like. The surface indicator or coating can be a clean thin film that can be put through an inkjet printer that includes or contains a dye or excitation additive. The printer prints the predetermined pattern or design on the film. When the film is installed on the component (e.g., the toilet seat, counter, etc.), the inkjet added image or predetermined pattern is now the indicator for validation of sanitization.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
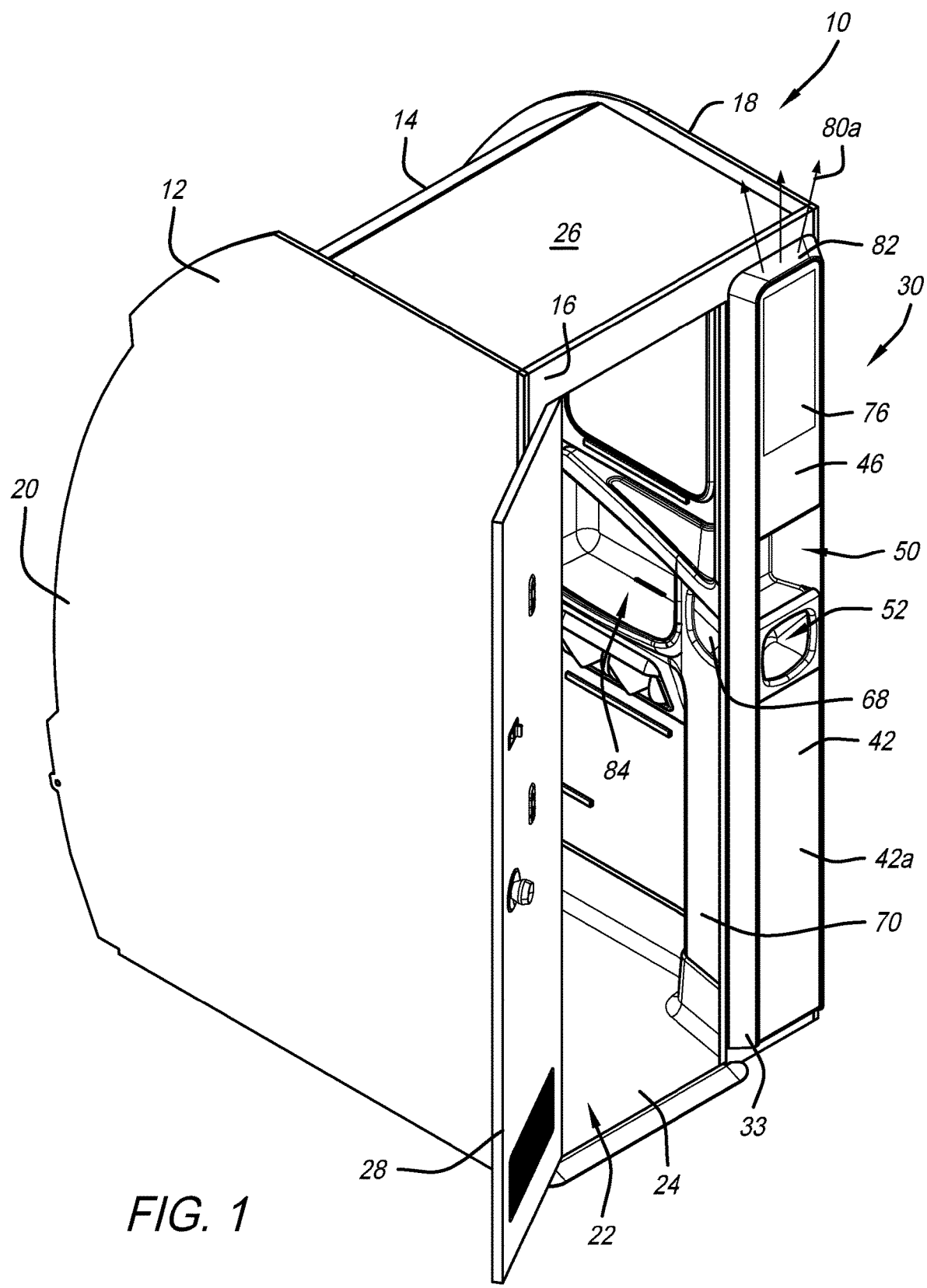
FIG. 1 is a perspective view of a lavatory monument assembly in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term: the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, the drawings show a lavatory monument assembly 10. As shown in FIG. 1, the lavatory monument assembly 10 generally includes an enclosure 12 that includes a plurality of walls (first wall 14, second wall 16, third wall 18 and fourth wall 20) that cooperate to define a lavatory interior 22. The enclosure 12 preferably also includes a floor 24, a ceiling 26 and an entry door 28 that is positioned on one of the plurality of walls. In the figures, the entry door 28 is shown positioned on the second wall 16. However, this is not a limitation and the door can be positioned on any wall.

Figure 2:
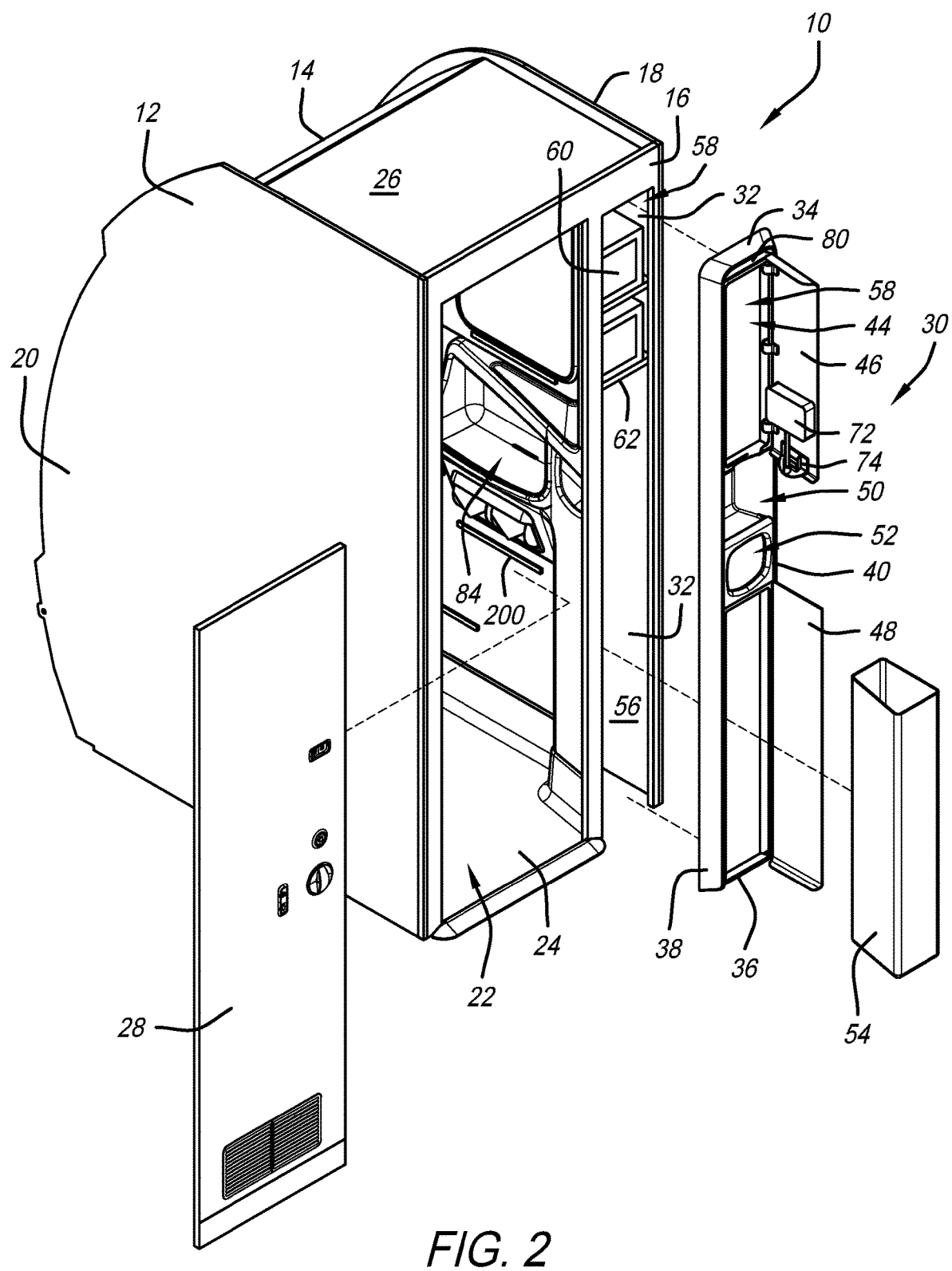
FIG. 2 is a partially exploded view of the lavatory monument assembly of FIG. 1.

As is shown in FIGS. 1-4, in a preferred embodiment, the lavatory monument assembly 10 includes a tower assembly 30 positioned on the second wall 16 adjacent to the entry door 28. In other embodiments, the tower assembly 30 can be positioned on any of the other walls. As shown in FIG. 2, access openings 32 (which can be one or more access openings and are referred to generally herein as a first access opening) are defined in the second wall 16 (or another wall, as necessary) and the tower assembly 30 is positioned over the first access opening 32. It will be appreciated that the first access opening 32 provides access to the lavatory interior 22 when one or more doors in the tower assembly are in the open position.

In a preferred embodiment, the tower assembly 30 includes a frame 33 that has a top wall 34, a bottom wall 36, a left side wall 38, and a right side wall 40. The tower assembly also includes a front wall 42 that includes a front surface 42a. The tower assembly 30 extends outwardly from the second wall 16 and defines a tower interior 44. Preferably, the tower assembly 30 also includes upper and lower or first and second doors 46 and 48 that are each movable between an open and a closed position. Preferably, a sanitizing recess 50 and an exterior trash recess or opening 52 are defined in the front surface 42a. The sanitizing recess 50 provides a user with access to hand sanitizer and the exterior trash opening 52 provides access to or is communicated with a trash receptacle 54 that is positioned in a trash receptacle space 56 in the lavatory interior 22, thereby allowing someone to place trash in the trash receptacle from outside the lavatory. In a preferred embodiment, the sanitizing recess 50 and the exterior trash opening 52 are positioned between the first and second doors 46 and 48. However, this is not a limitation and in another embodiment, and the sanitizing recess 50 and/or the exterior trash opening 52 can be positioned above or below either of the first and second doors.

As shown in FIG. 2, in a preferred embodiment, the first door 46 provides access to a wipes storage space 58 that is located at least partially in the lavatory interior 22 (and may be located also at least partially in the tower interior) and the second door 48 provides access to the trash receptacle space 56 that is located at least partially in the lavatory interior 22 (and may be located also at least partially in the tower interior). In another embodiment, the first door can provide access to both the wipes storage space and the trash receptacle space. As shown in FIG. 2, the wipes storage space 58 may include space for multiple types of wipes 60, such as paper towels, sanitizing wipes, etc. and may include shelves 62 for placing the wipes containers thereon. It will be appreciated that the first and second doors 46 and 48 provide access to the trash receptacle 54 and the different types of wipes 60 from the exterior of the enclosure/lavatory.

Figure 3:
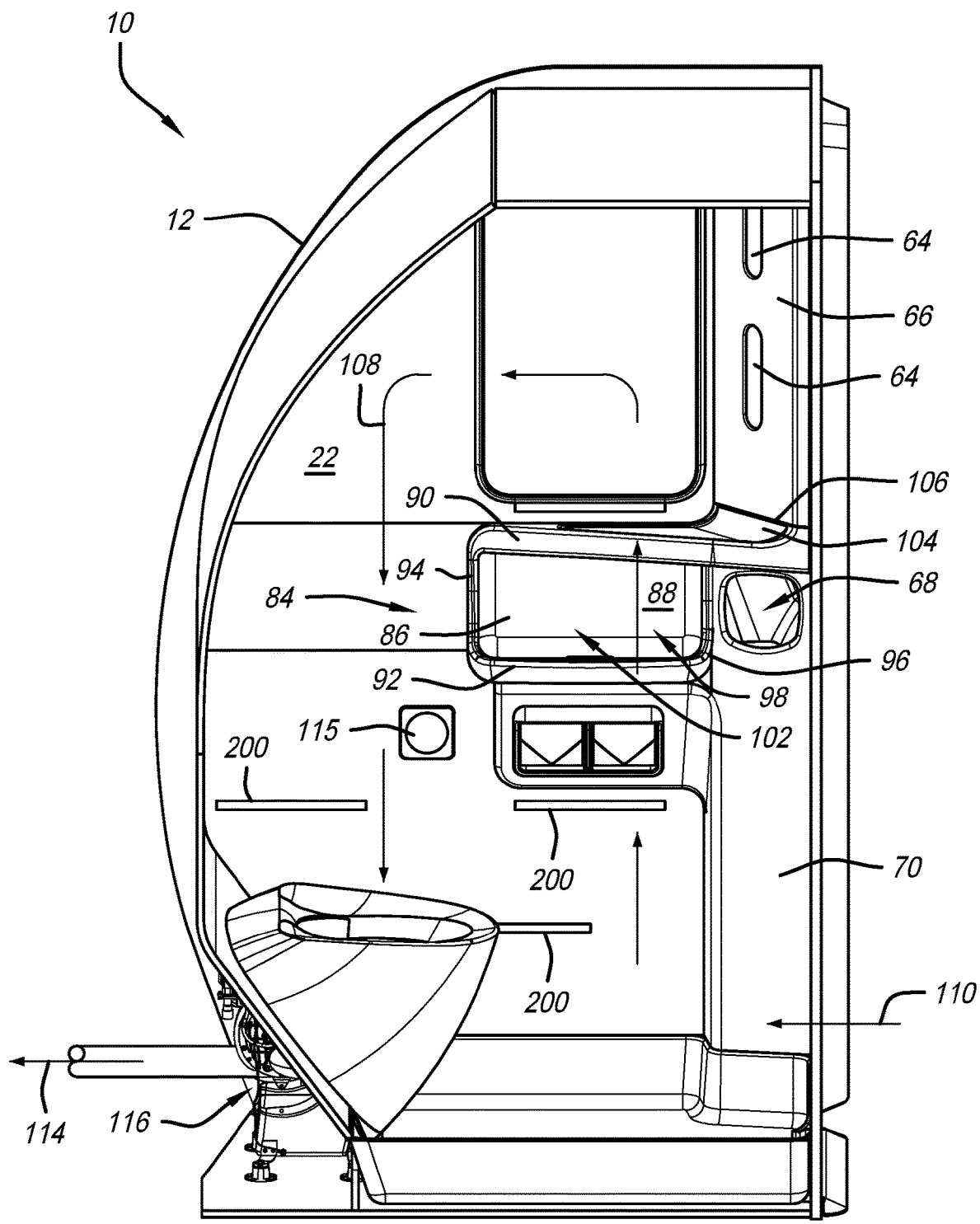
FIG. 3 is a side elevational interior view of the lavatory monument assembly of FIG. 1.

As shown in FIG. 3, one or more wipes dispensing openings 64 are defined in a wipes panel 66 in the lavatory interior and an interior trash opening 68 is also located or defined in a trash panel 70 in the lavatory interior 22. The wipes panel 66 at least partially defines the wipes storage space 58 and the trash panel 70 at least partially defines the trash receptacle space 56.

As shown in FIG. 2, in a preferred embodiment, the first door 46 provides access to a sanitizer dispenser 72 positioned in the tower assembly 30 that is configured to dispense hand sanitizer into the sanitizing recess 50. See the sanitizer outlet 74 in FIG. 4. The sanitizer dispenser 72 can be positioned on the door or in space defined within the tower interior 44. The sanitizer dispenser 72 can dispense liquid hand sanitizer (e.g., using a touchless sensor) when a user places their hand(s) into the appropriate location within the sanitizing recess 50 or the sanitizing dispenser can include sanitizing wipes that can be accessed by a user within the sanitizing recess.

In a preferred embodiment, the tower assembly 30 includes a display screen 76 for providing information to passengers and crew. The display screen 76 can be located anywhere on the tower assembly 30. In a preferred embodiment, the display screen 76 is located on the first door 46. The information provided by the display screen 76 can include, for example, one or more of the vacancy state of the lavatory, the sanitization level air status in the lavatory (e.g., how long since the air in the lavatory was last replenished), how long since the lavatory surfaces were cleaned, information regarding the sanitizing measures taken to keep the lavatory clean, etc.

Figure 4:
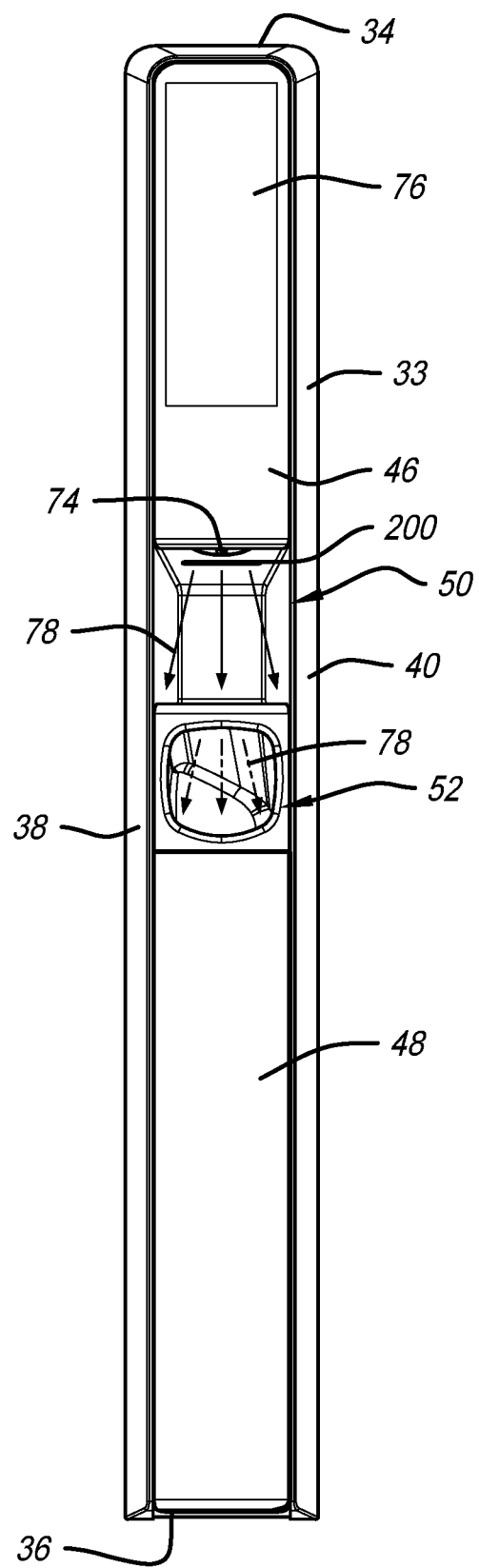
FIG. 4 is a front elevational view of the tower assembly.
Figure 5:
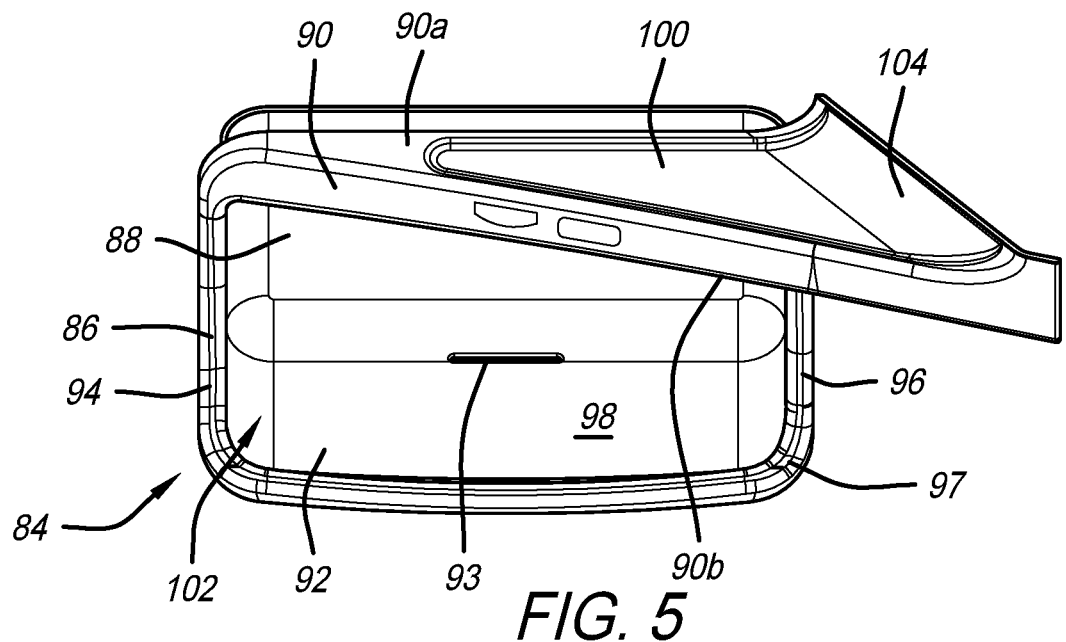
FIG. 5 is a top perspective view of the sink basin assembly.
Figure 17:
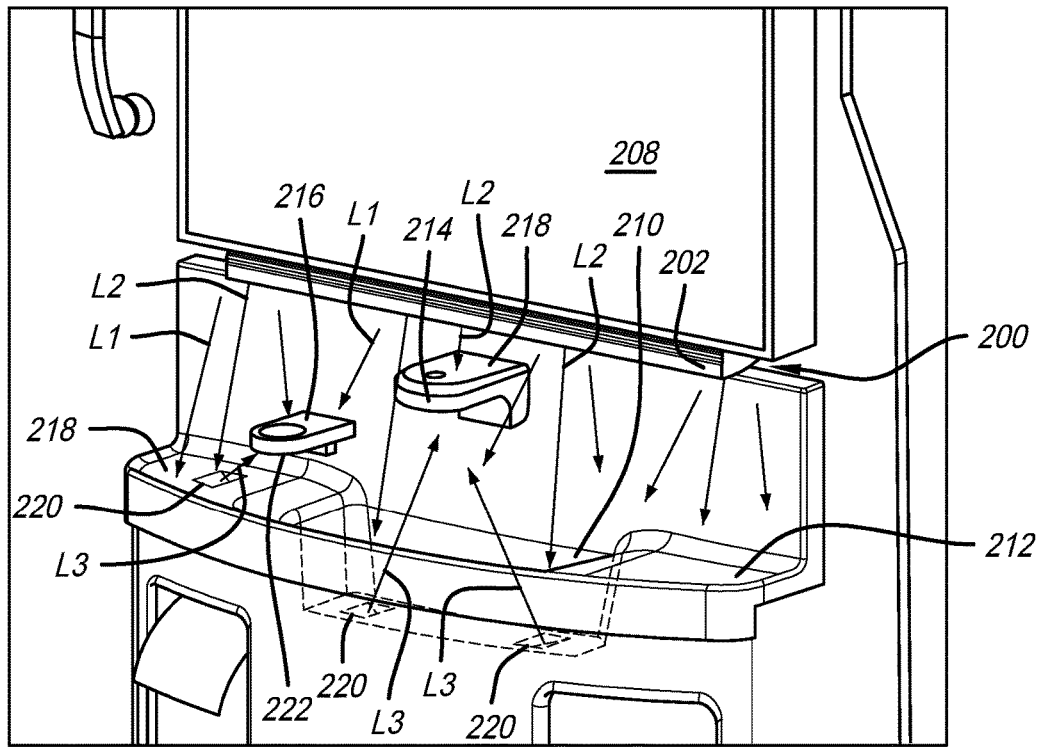
FIG. 17 is a perspective view of the light assembly as part of the UV sanitization system.

As shown in FIG. 4, in a preferred embodiment, both the sanitizing recess 50 and the exterior trash opening 52 can include at least one UV light source 78 therein for sanitizing the interior surfaces of the sanitizing recess 50 and/or the exterior trash opening 52. In a preferred embodiment, the UV light source can be the light assembly 200 discussed below and can include reflective surfaces 220 and the like as shown in FIG. 17.

In a preferred embodiment, the tower assembly 30 includes indication lighting that is emitted from the tower to indicate to passengers whether the lavatory is in a "replenished state" or an "unreplenished state," (or in a "sanitized state" or "unsanitized state") as further described below. The indication lighting can be any or all of trim lighting around the frame 33, light emitting from the sanitizing recess 50 or exterior trash opening 52, the color of the display screen 76 or a light 80 positioned at the top of the tower that, when the lavatory monument is positioned in an aircraft, washes or shines on the ceiling to provide indication of the status of the lavatory from throughout the cabin. Light 80 is shown in FIG. 2 positioned under the top wall 34 of the tower assembly, which can include a lens or transparent cover 82 therein for the light to shine through (see the light emission lines 80a in FIG. 1).

As a result of the indication lighting, the tower assembly 30 includes a first indication state that indicates that the air in the lavatory interior 22 is in a replenished or sanitized state and a second indication state indicates that the lavatory interior 22 is in an unreplenished or unsanitized state. In short, when the tower assembly 30 emits the selected color it indicates to the passengers that the lavatory is ready to be entered and that the air has recently completed a clean air replenishment (and/or the lavatory has completed a UV sanitization cycle). Any colors for the first and second indication states are within the scope of the present invention. For example, green or cyan can be used to indicate the replenished, sanitized or clean state and red can be used to indicate the unreplenished, unsanitized or dirty state. In another embodiment, the tower assembly 30 and/or the indication lighting emanating therefrom can be provide more than two indication states and different colors can be provided for each. For example, the tower assembly can indicate that the lavatory is occupied or not occupied, the lavatory needs maintenance, the trash needs to be emptied, flight attendant help is needed by the lavatory occupant, etc. Therefore, if the tower assembly includes five indication states, each indication state is assigned a different color.

As shown in FIGS. 1-3 and 5-8, in a preferred embodiment the lavatory monument assembly 10 includes a wash or sink basin assembly 84 positioned in the lavatory interior 22. In a preferred embodiment, the sink basin assembly 84 includes a sink basin 86 that includes a back wall 88, a top wall 90, a bottom wall 92 with a drain 93 therein, a first side wall 94, and a second side wall 96 that cooperate to defined a sink basin interior 98. The top wall 90 includes a top surface 90a and a bottom surface 90b. The bottom surface 90b partially defines the sink basin interior 98, and wherein the top surface 90a is a counter 100. In a preferred embodiment, the sink basin 86 includes a mouth 102 or opening through which a user places their hands to enter the sink basin interior 98 that is oriented generally vertically. In a preferred embodiment, the leading or front edge of the sink basin 86 is shaped to provide a handle for passenger stability during turbulence. As shown in the drawings, the front edges of the bottom wall 92, first side wall 94, and second side wall 96 can include a handle portion 97 extending therearound that is thicker than the remainder of the wall and that can be grabbed by a user when necessary.

Figure 6:
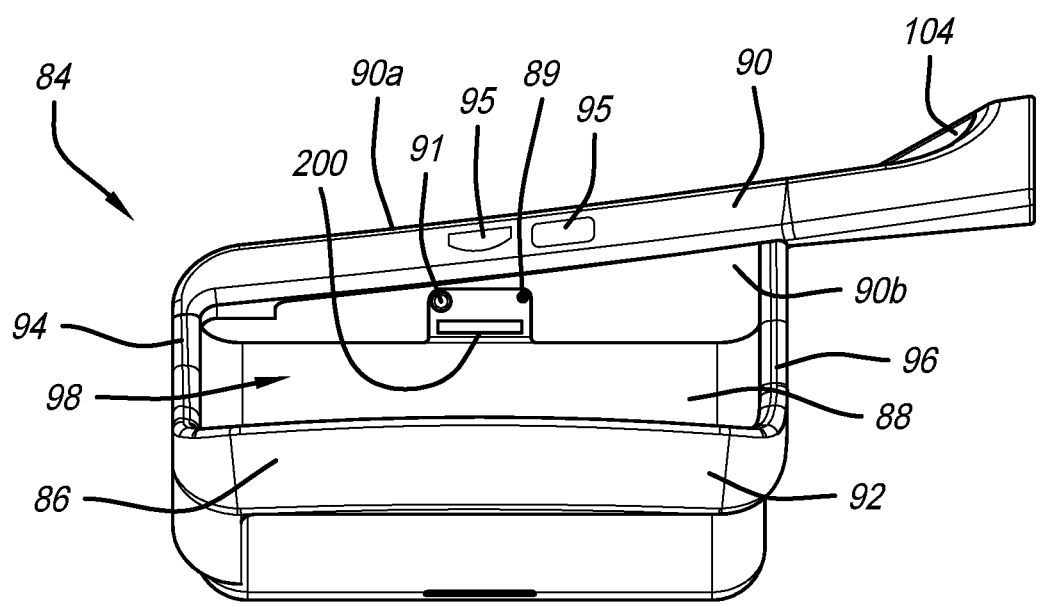
FIG. 6 is a bottom perspective view of the sink basin assembly.

As is shown in FIG. 6, associated with the bottom surface of the top wall 90 is a motion activated water dispenser 91 (faucet) and a motion activated soap dispenser 89 that dispense soap or water when a user places their hands in the appropriate location within the wash basin interior (see icons 95 in FIG. 6 that are aligned with the soap and water dispensers). The dispensers can be located on the bottom surface of the top wall or on the chassis 101 discussed below. FIG. 6 also shows a UV light source for sanitizing the sink basin, which may be the light assembly 200 discussed herein. Reflective surfaces 220 (discussed further below) can also be included in the sink basin 86.

Figure 7:
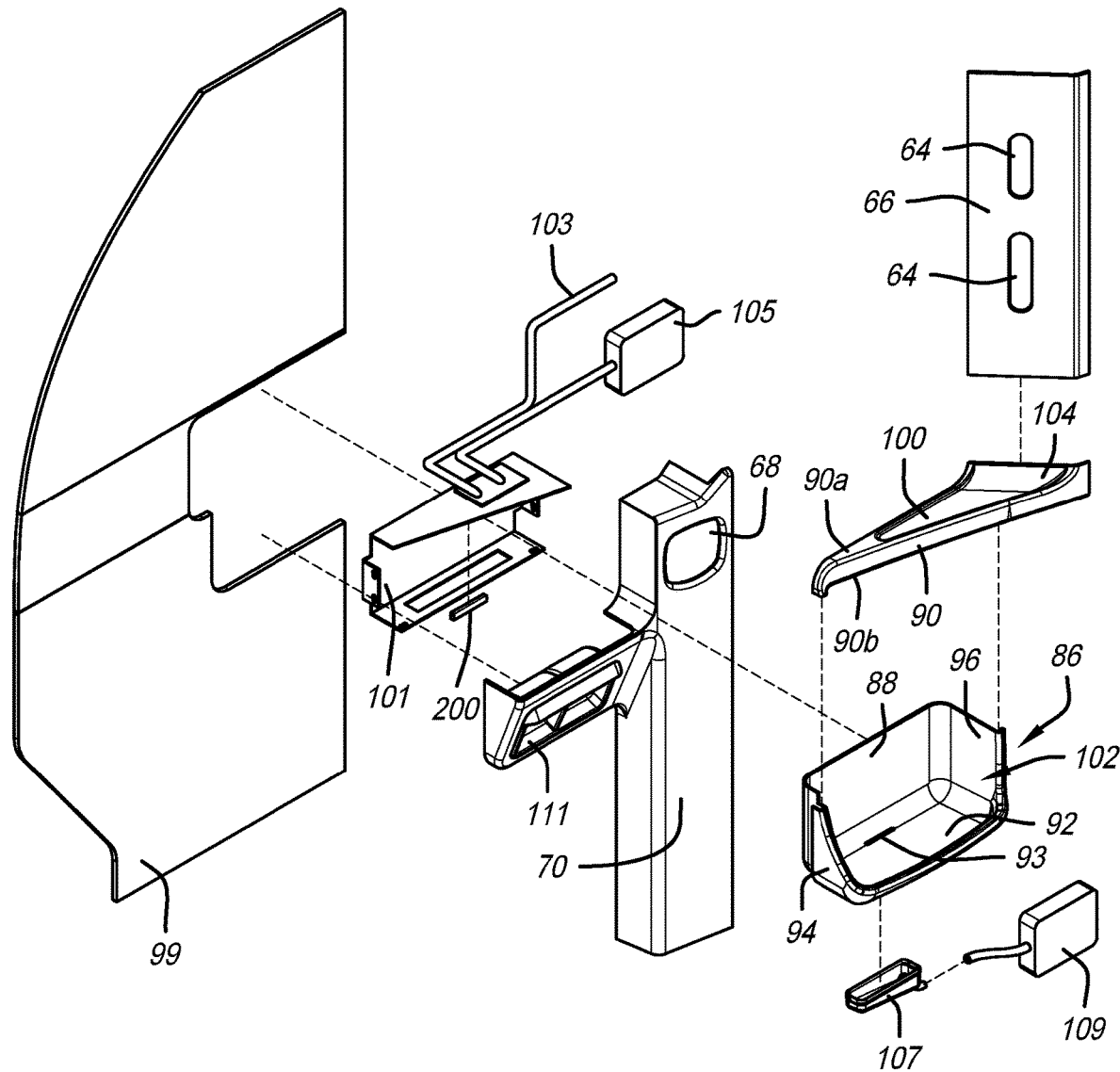
FIG. 7 is an exploded perspective view of the sink basin assembly and other components.

FIG. 7 is an exploded view of the sink basin assembly 84 and related components. In a preferred embodiment, many of the components are easily removable for deep cleaning. The sink basin assembly 84 includes a chassis 101 that is mounted to a wall or interior wall 99 of the enclosure. Water and soap are routed to the water and soap dispensers 91 and 89. Water can be routed via pipe 103 and soap from soap reservoir 105. However, these are only exemplary and water and soap can be routed to the dispensers in any known way. A container 107 for routing water to a storage tank 109 (e.g., a gray water storage tank) or the like can be located under the drain 93. A toilet paper console 111 is located under the sink basin 86 and may be attached to the trash panel 70.

Figure 8:
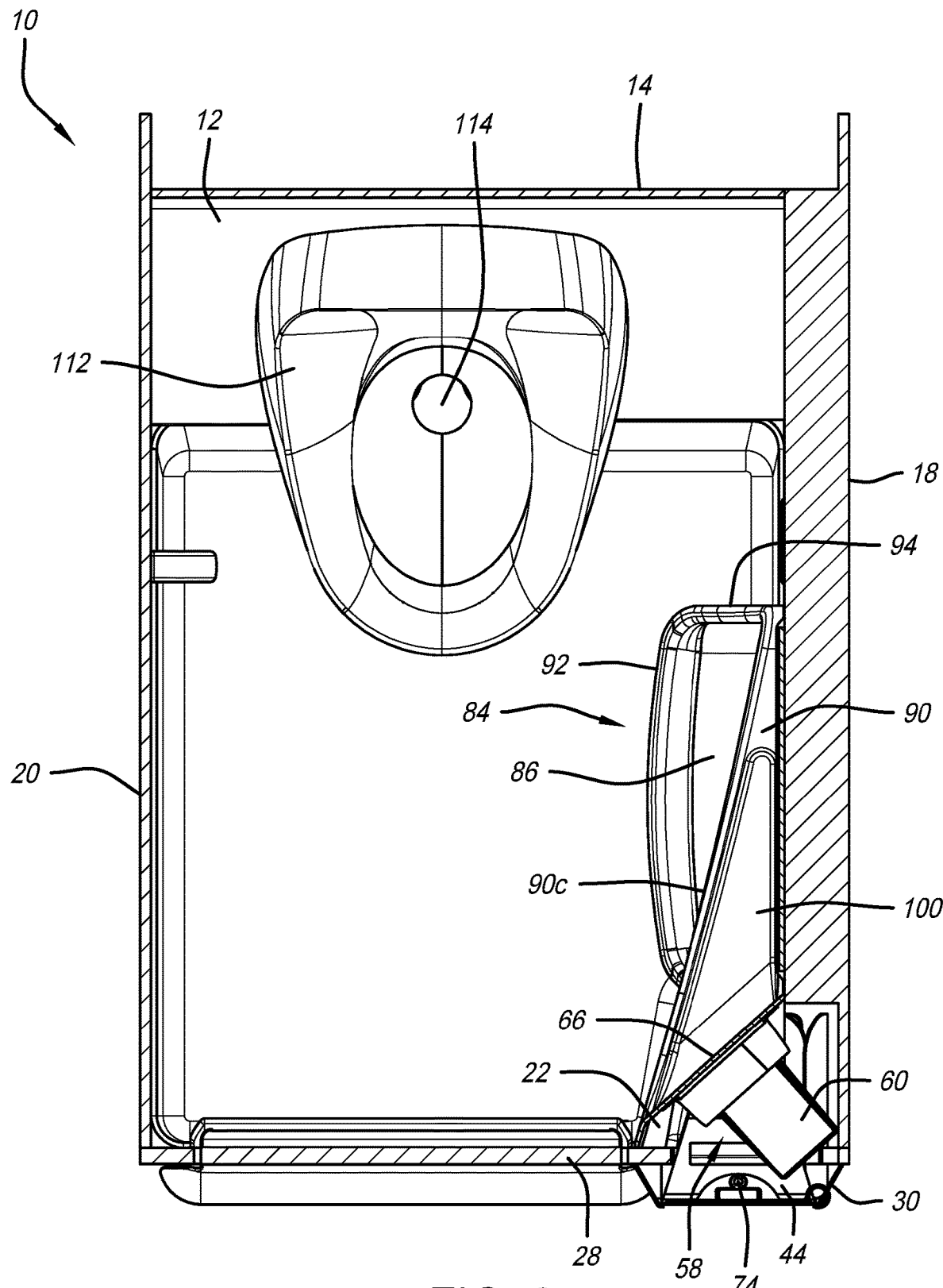
FIG. 8 is a top plan cross-sectional view of the lavatory monument assembly of FIG. 1.

As is best shown in FIG. 8, in a preferred embodiment, the top wall 90 (and, therefore, counter 100) angles inwardly from adjacent the entry door 28 toward the third wall 18 (see the front surface 90c in FIG. 8). As a result, at least a portion of the front edge of the bottom wall 92 of the sink basin 86 extends beyond the front edge of the top wall 90. FIG. 8 also shows how a portion of the wipes storage space 58 can be located in the lavatory interior 22 (i.e., inside of the second wall) and a portion of the wipes storage space 58 can be located in the tower interior 44. As shown, the wipes dispenser 60 extends into the tower interior 44. This also applies to the trash receptacle space.

In a preferred embodiment, the top wall 90 (and/or counter 100) of the sink basin 86 includes a curved portion or surface 104 that meets and is relatively flush with the wipes panel 66. Preferably, the joint or groove 106 between where the top edge of the curved surface 104 and bottom edge of the wipes panel 66 meet is vertically oriented, thus preventing dirt from building up therein. As used herein, "meet" means that the edges may contact one another or may be closely adjacent to one another.

As shown in FIGS. 3 and 9-13, in a preferred embodiment, the lavatory monument assembly 10 includes an air replenishment system 108 that provides the ability to replenish or clean the air in the lavatory interior 22 when desired (e.g., at predetermined intervals, when a button is pushed or switch is activated, when a certain action takes place, such as a user exiting the lavatory, etc.). The lavatory and air replenishment system can indicate the air status of the air in the lavatory interior and may include a "replenished state" and an "unreplenished state." In the replenished state, the lavatory is considered usable by a passenger or a passenger may enter the lavatory. In the unreplenished state, the lavatory is not considered usable by a passenger or a passenger should not enter the lavatory. In a preferred embodiment, the air replenishment system is actuated each time a user exits the lavatory. Therefore, after a user exits the lavatory, the air volume in the lavatory interior is in the unreplenished state and after the air replenishment system is actuated the air volume in the lavatory interior is in the replenished state. As described below, the actuation of the air replenishment system can be automated or can be actuated by the pressing of a button or other manual switching action. After a predetermined period of time, the system may consider the air to be in the unreplenished state. For example, if the lavatory goes unused for fifteen minutes the air in the lavatory may need to be replenished. In an automated system, the air replenishment system would actuate and switch back to a replenished state. In a manual system, the indication state may change (e.g., beacon light 80 or other lights on the tower assembly 30 may change from green to red or the indicator lights 130 discussed below may change from green to red), thus requiring a user to press the button to replenish the air in the lavatory. In a preferred embodiment, the entry door may lock if the air is in an unreplenished state.

Figure 9:
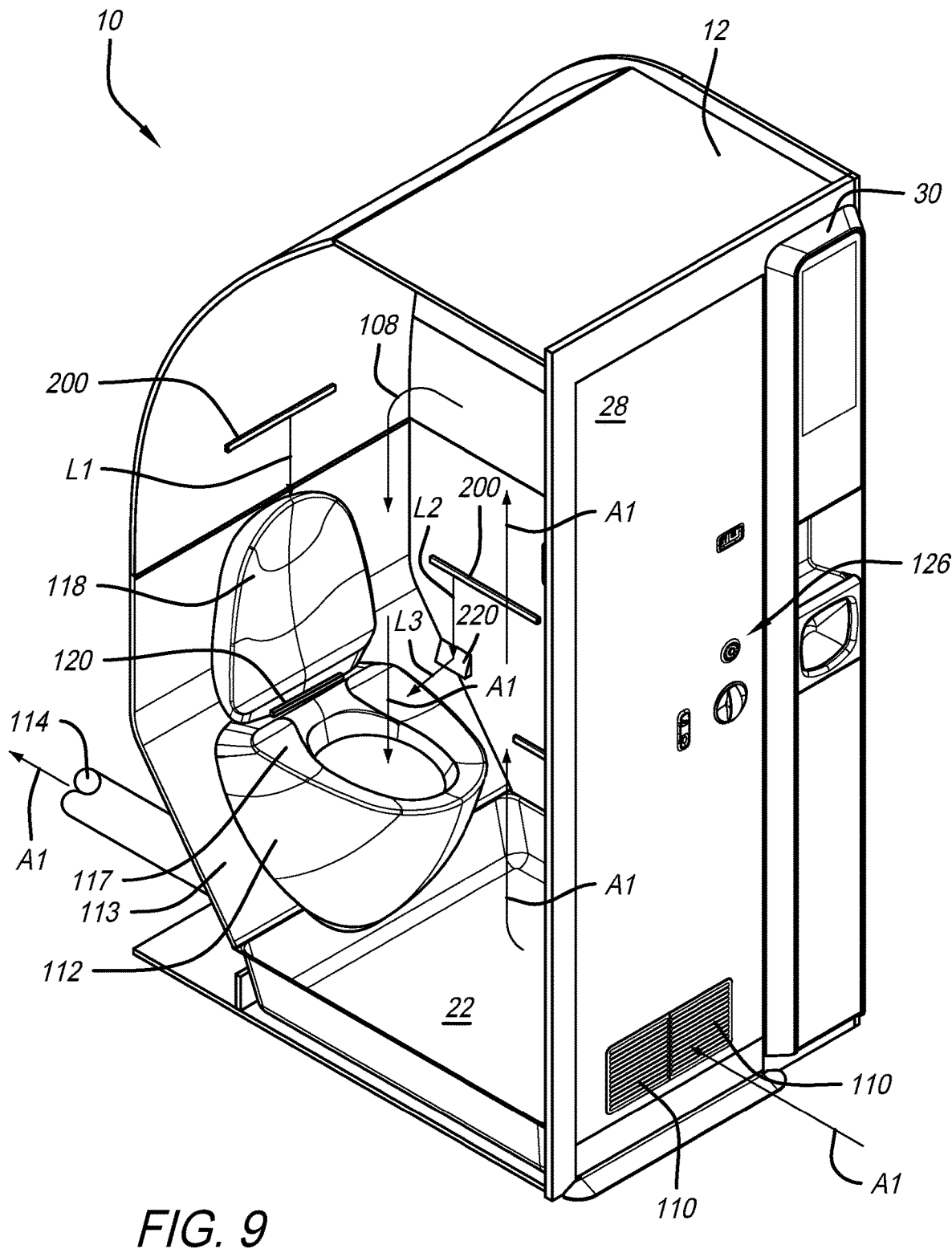
FIG. 9 is a perspective view of the lavatory monument assembly of FIG. 1 with a wall removed.

The enclosure 12 includes an inlet 110 for entry of air from the exterior of the enclosure (e.g., the cabin interior, the ECS or environmental control system, etc.). The inlet 110 can be located anywhere in the lavatory monument assembly 10 (e.g., in any of the plurality of walls, the ceiling, the floor, etc.). As shown in FIG. 9, in a preferred embodiment, the inlet(s) 110 or decompression vents are located in the entry door 28.

A toilet 112 that includes an outlet 114 is positioned in the lavatory interior 22. The outlet or a valve therein includes an open and a closed state. When the outlet 114 is in the open state the lavatory interior 22 is fluidly communicated with an exterior of the lavatory monument assembly 10 or the enclosure 12 such that the air in the lavatory interior can be pulled or sucked therefrom. A vacuum system 116 (see FIG. 3) is preferably used to pull the volume of air in the lavatory interior 22 out of the enclosure 12. In a preferred embodiment, the same air vacuum system 116 that is used to flush the toilet can be used or repurposed to pull the air out of the lavatory interior through the outlet 114 or toilet bowl opening. In a preferred embodiment, the toilet seat and/or toilet seat cover 118 are in the open position when the air is pulled out of the outlet. In this embodiment, the toilet seat and/or cover 118 is automated such that it can be opened or moved to the open position prior to the current volume of air in the lavatory interior being pulled or sucked out the outlet 114. Therefore, in a preferred embodiment, the system opens the toilet seat and/or cover whenever the system is activated. In a preferred embodiment, to open the toilet seat, a solenoid within the toilet lid hinge dampener mechanism 120 is activated, and is then deactivated when the air cycle is complete thus allowing the lid or cover 118 and/or seat to close.

As shown in FIG. 9, when the system is actuated, the volume of air in the enclosure is pulled through the open outlet 114 (see arrows A1 in FIG. 9). At the same time, air from outside of the enclosure 12 is pulled through the inlet 110 to replace the volume of air that just exited. The air present in the lavatory interior prior to actuation of the system may be referred to herein as a first volume of air and the air present in the lavatory after actuation of the system that comes in through the inlet may be referred to herein as a second volume of air or replenished air.

Figure 10:
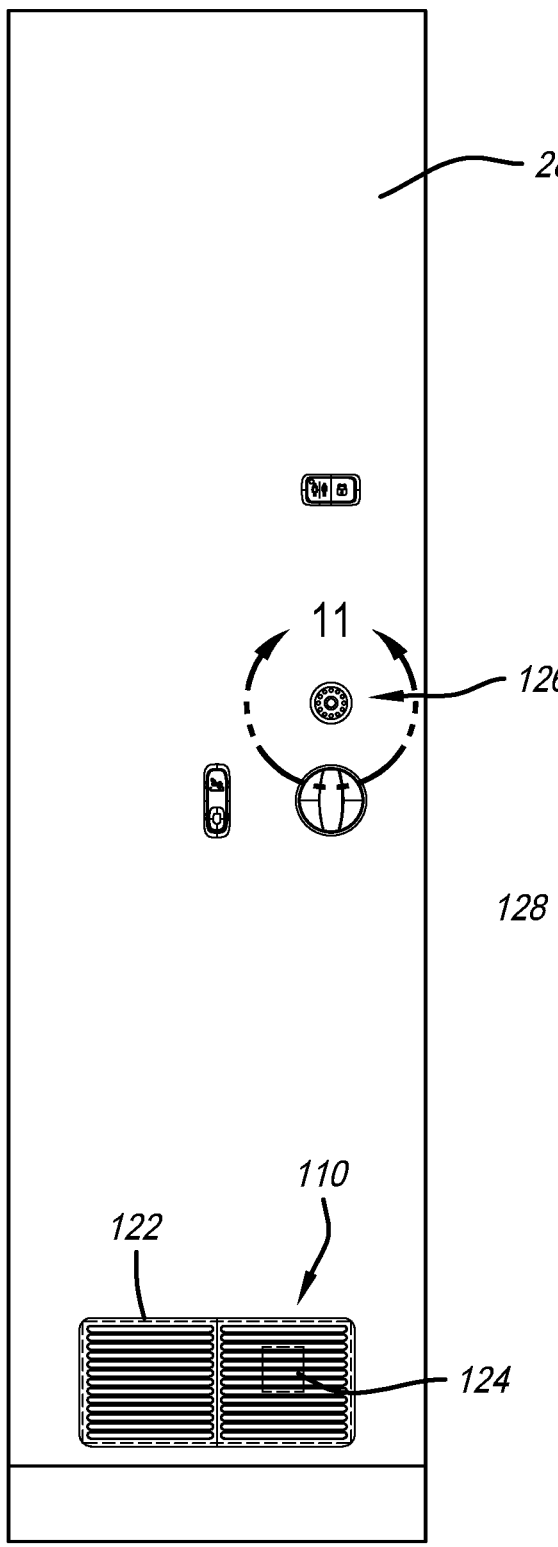
FIG. 10 is a front elevational view of the entry door.

As shown in FIG. 10, in a preferred embodiment, the inlet 110 includes a filter 122 (such as a HEPA filter therein) through which the air passes as it enters the lavatory interior. In another preferred embodiment, the inlet 110 can include an air freshener 124 positioned therein through which the air passes as it enters the lavatory interior.

The air replenishment system 108 can be actuated at predetermined intervals, when a button is pushed and/or switch is activated. In a preferred embodiment, the air replenishment system 108 can only be actuated when no one is in the lavatory and when the entry door 28 is closed. In an embodiment, the air replenishment system 108 cannot be actuated when the entry door 28 is locked because the lavatory is typically only locked when a person is in the lavatory. However, the system may also automatically lock the door when an air replenishment cycle is about to occur in order to prevent the entry door from being opened during the cycle. In a preferred embodiment, the lavatory enclosure includes a sensor or detector for determining when a person is in the lavatory.

Figure 11:
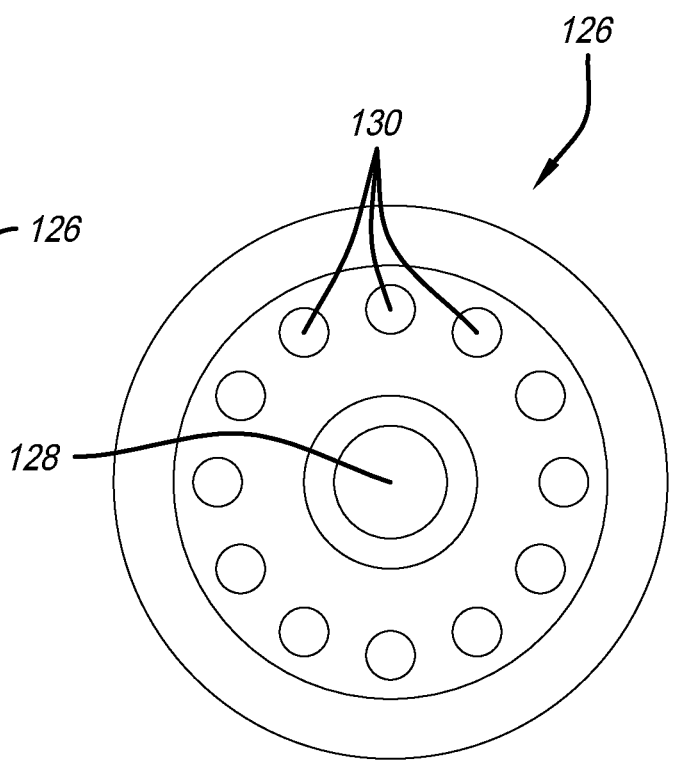
FIG. 11 is a front elevation view of the activation assembly.

As shown in FIGS. 10-11, in a preferred embodiment, the air replenishment system 108 includes an activation assembly 126 that includes a manual activation button 128 and a plurality of indicator lights 130 encircling or surrounding the button 128. The indicator lights 130 are visual indicators that surround the button 128 and can change color or turn on/off in a ring pattern to communicate information to crew and/or passengers. The button can be any type of switch configured to actuate the system and replenish the air. The lights can be LEDs or other types of lights. The lights can also be arranged in a line or other shape. In a preferred embodiment, the lights 130 are an indication system that is configured to indicate the air status of the lavatory interior 22. The lights can be programmed to change colors between the replenished and unreplenished states. The lights can be solid in the replenished state and blink or be off in the unreplenished state. In another embodiment, the lights may act as a timer to show how long it has been since the air was replenished. For example, the lights may all be green to show the air was just replenished. Thereafter, for each minute (or other predetermined period of time) that passes, one of the lights may turn red (or the light may turn off). Different passengers may want to push the button 128 to replenish the air based on how many red or off lights are present. It will be appreciated that the amount of time since the previous replenishment may also be indicated on the display screen 76 (e.g., "10 minutes since last air replenishment" may be displayed on the screen).

Figure 12:
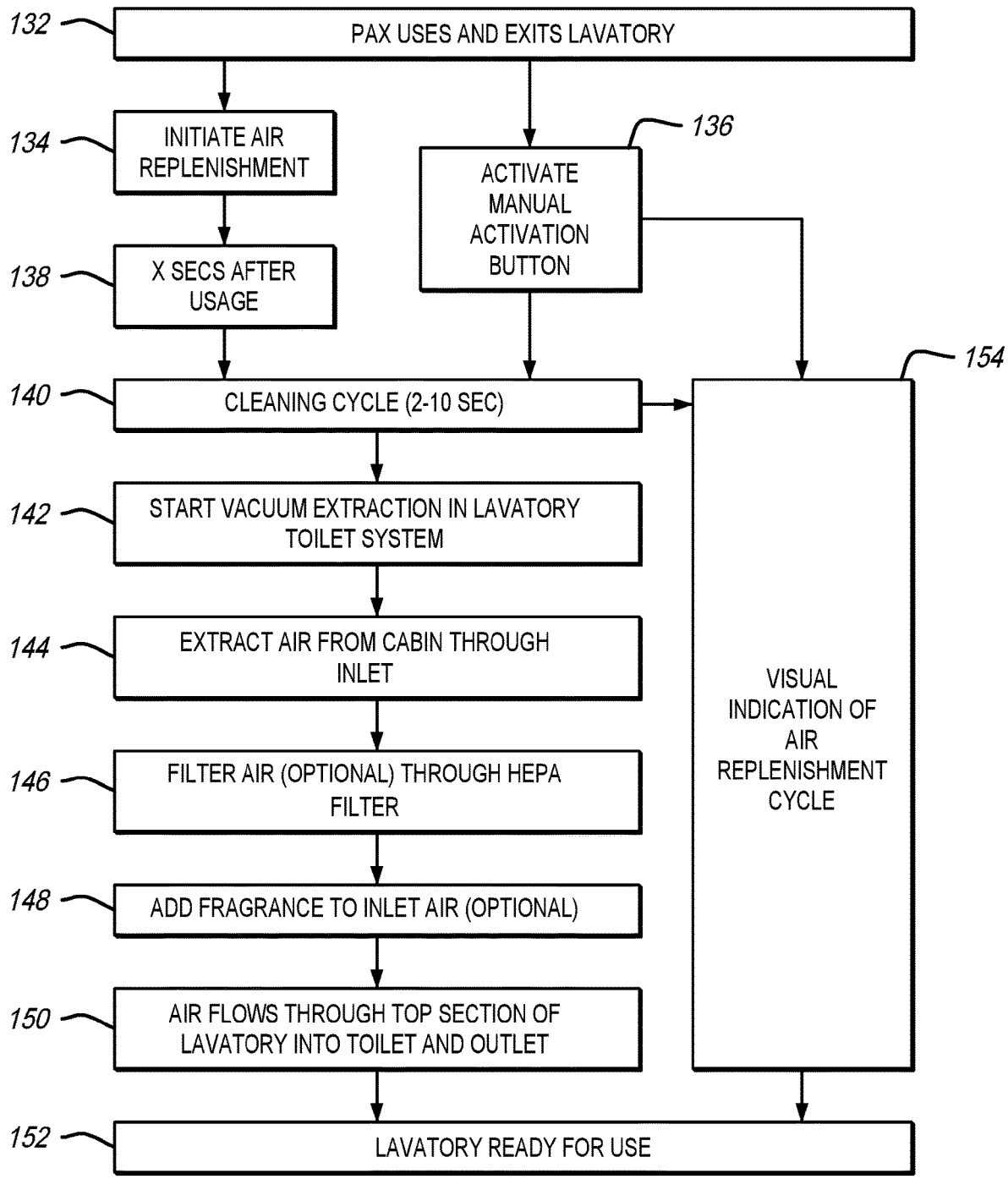
FIG. 12 is a flow chart showing exemplary steps of the air replenishment system.

FIG. 12 is a flow chart showing use of the air replenishment system 108. As shown, two different actions can take place after a passenger (abbreviated pax, as is known in the art) uses and exits the lavatory (step 132), the automated step of initiating air replenishment (step 134) on the left or the manual action of pushing or activating the manual activation button (step 136) on the right. In a preferred embodiment, the automated action of beginning the cleaning cycle (step 140) begins a predetermined number (x) seconds after usage of the lavatory (step 138). This may be x seconds after the door is unlocked, x seconds after the door closes, x seconds after the sensor in the lavatory senses that no person is in the lavatory interior or x seconds after another predetermined event. Activation of the manual activation button 128 also causes the cleaning cycle to begin (step 140). The system may include both the automated and the manual option or one or the other. FIG. 12 includes an exemplary "(2-10 sec")", indicating that the cleaning cycle step takes 2-10 seconds. However, this is not a limitation and the replenishment cycle (pulling or moving the first volume of air out of the outlet and the second volume of air through the inlet) may take longer (e.g., 2-60 seconds), but preferably takes under 30 seconds. During the cleaning or air replenishment cycle, the following steps may occur: Start vacuum extraction in lavatory toilet system (step 142), extract air from cabin through inlet (step 144), filter air through HEPA filter (which is optional) (step 146), add fragrance to inlet air (which is optional) (step 148), the air flows through the top section of the lavatory interior and into the toilet and through the outlet (step 150) and then the lavatory is ready for use (step 152).

FIG. 12 also shows that while some of the above steps are occurring, the activation assembly 126 (and the indicator lights 130 thereof) can indicate that the air replenishment or clean air cycle is occurring (step 154). For example, the lights can turn on and off in a circular pattern to indicate that the air replenishment system is working (similar to the indicator on a computer screen that a program is working) or the lights can blink on and off to indicate that the air replenishment system is working or in progress. This progress indication can also be shown on the display and/or indicated by the wash lights (e.g., 80).

Figure 13:
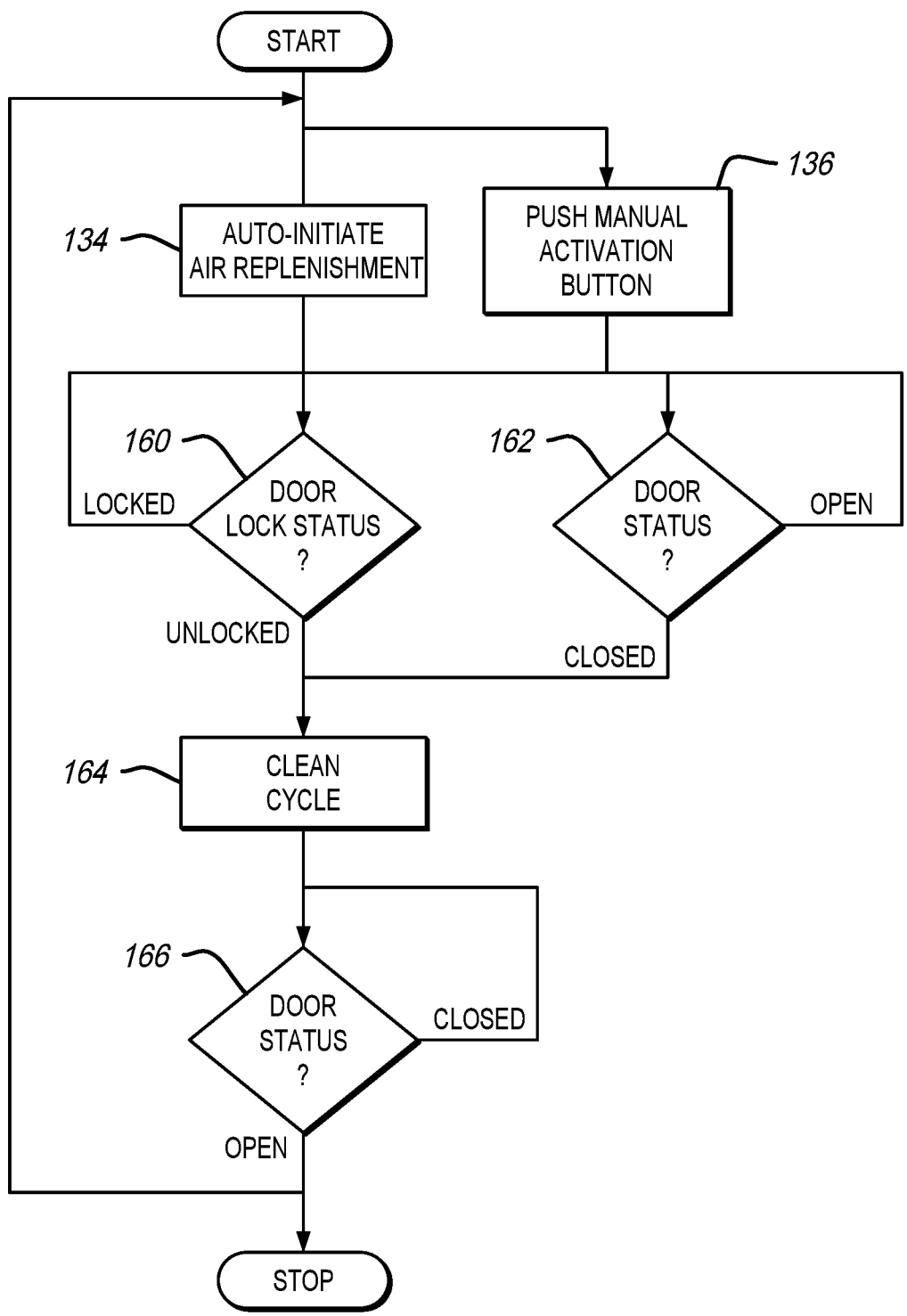
FIG. 13 is a flow chart showing exemplary steps of the air replenishment system.

In accordance with a preferred embodiment of the present invention, FIG. 13 shows another flow chart or decision tree related to when the "clean cycle" or air replenishment (or UV sanitizing discussed below) may occur. In a preferred embodiment, the clean cycle only occurs when a passenger is not in the lavatory. Therefore, the system determines if a passenger is in the lavatory. This is done both after the initiation of air replenishment automatically (step 134) (e.g., after a predetermined period of time has passed and the system is ready to replenish the air) or after pushing of the manual activation button (step 136). The system queries whether the door is locked or unlocked (step 160) and whether the entry door is closed or open (step 162). If the door is locked, the system assumes is passenger is in the lavatory and the system continues to query until the door is unlocked. Therefore, when a passenger pushes the manual activation button 128 when the door is locked, nothing will occur. If the door is open, the system continues to query until the door is closed. When both the door is unlocked and closed, the system can perform the clean cycle (step 164). Once the door is opened again (step 166), the system resets (assuming another passenger is entering the lavatory).

In a preferred embodiment, the air replenishment system includes software and/or a controller (associated with the lavatory or centrally located in the aircraft) that controls the operation of the system. The above discussed flow charts and/or decision tree can be associated with the software and/or controller.

As shown in FIGS. 14-17B, in a preferred embodiment, the aircraft lavatory monument 10 includes a UV sanitization system that sanitizes certain surfaces within the lavatory at predetermined intervals or after each use of the lavatory by a passenger. The UV sanitization system includes lenses that direct the UV light at specified angles toward surfaces to be sanitized (referred to herein as "direct surfaces to be sanitized") and toward specific surfaces that are coated with a UV reflective material that in turn direct the light rays toward other surfaces to be sanitized (referred to herein as "indirect surfaces to be sanitized"). The UV sanitization system may be associated with the air replenishment system above or the UV sanitization system may be separate from the air replenishment system, but may operate similarly (e.g., the system may be activated after lavatory use or when a button is pushed). Accordingly, all description related to the operation of the air replenishment system (e.g., the flow charts, etc.) applies to the UV sanitization system.

Figure 14:
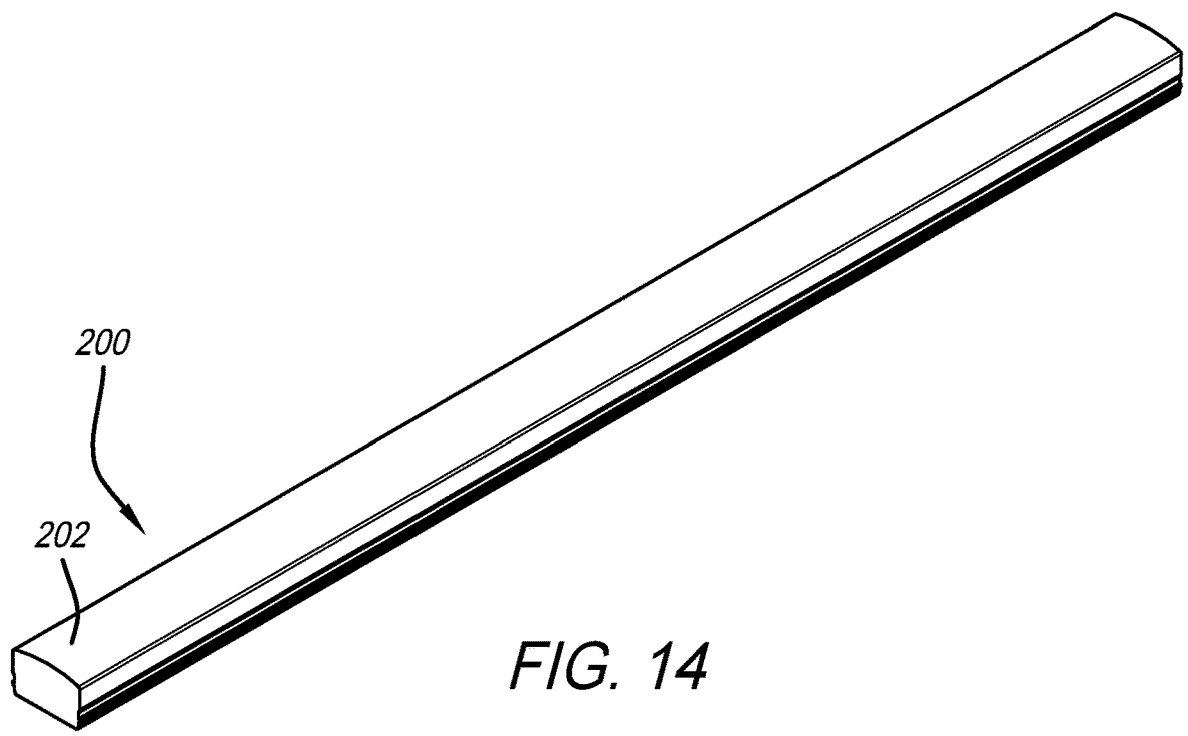
FIG. 14 is a perspective view of the light assembly.
Figure 15:
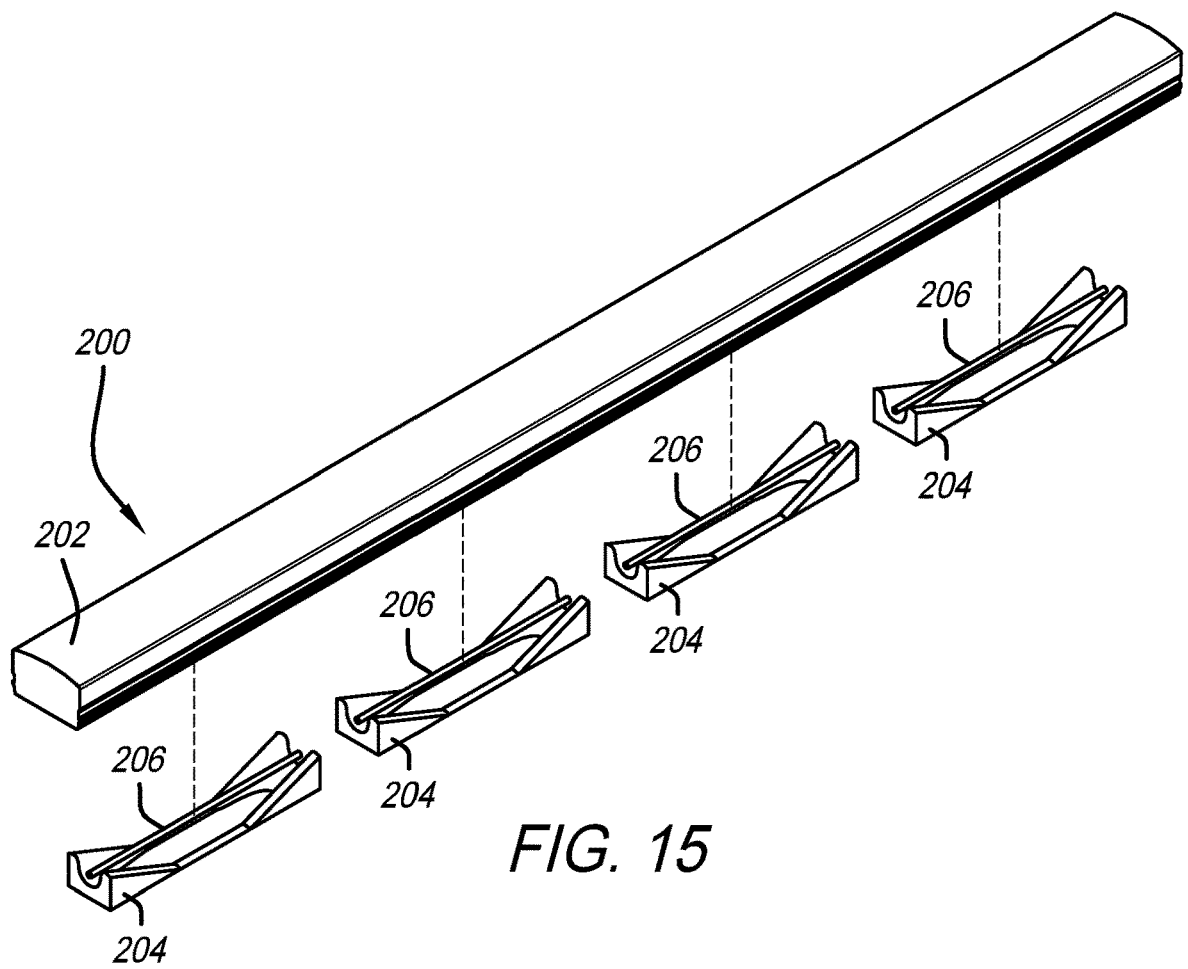
FIG. 15 is an exploded perspective view of the light assembly.
Figure 16:
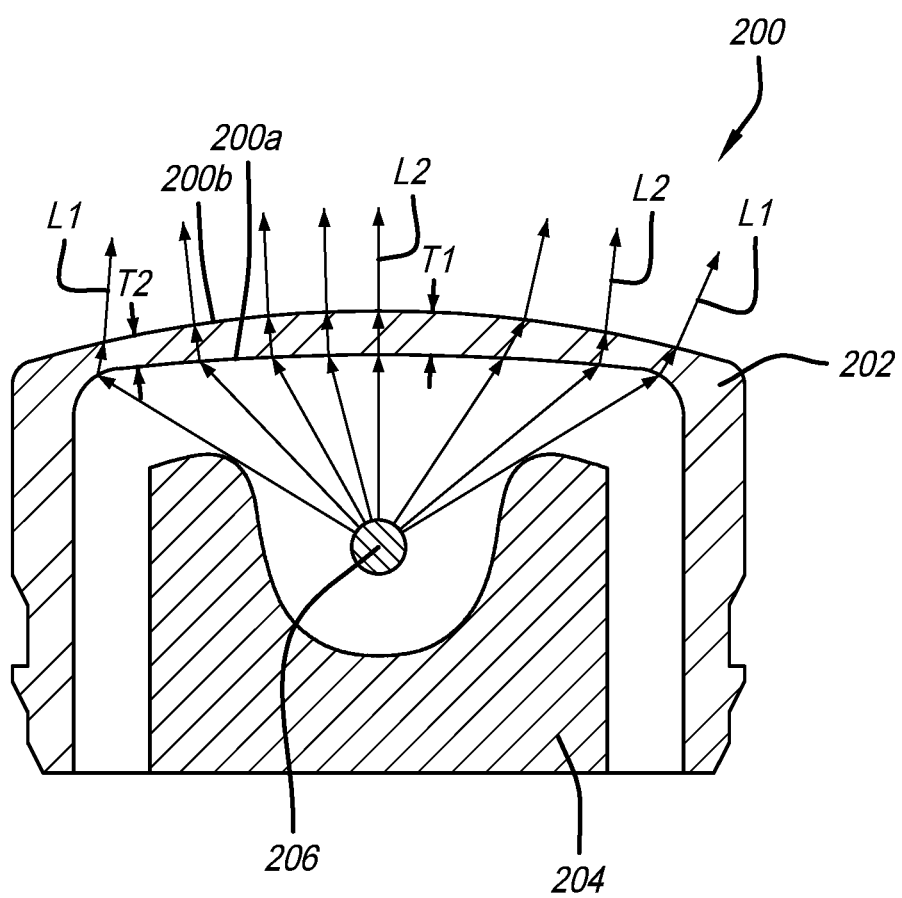
FIG. 16 is a cross-sectional view of the light assembly.

FIGS. 14-16 show an exemplary light assembly 200 that includes a lens member 202, and one or more fixtures 204 that include UV light sources 206 therein. FIG. 16 shows a cross section of the light assembly 200 and includes a plurality of light rays extending from the UV light source 206. The lens member 202 includes surface geometry that directs the light rays as needed toward the direct surfaces to be sanitized. As shown, some light rays may not change direction as they pass through the lens member 202, while others may refract or change direction or be angled as they pass through the lens member 202, based on the geometry of the lens. The lens member includes a first surface 200a, a second surface 200b and a thickness. The thickness changes as is needed to direct the light rays, as desired. See, e.g., first thickness T1 and second thickness T2 in FIG. 16.

Figure 17A:
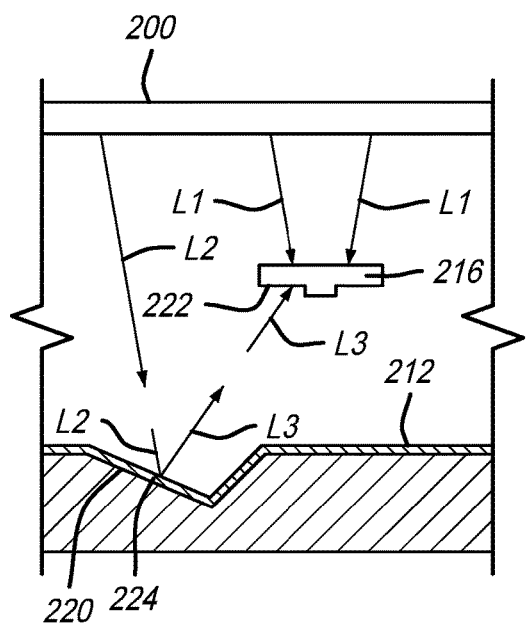
FIG. 17A is a schematic view showing an exemplary reflective surface from the UV sanitization system of FIG. 17.
Figure 17B:
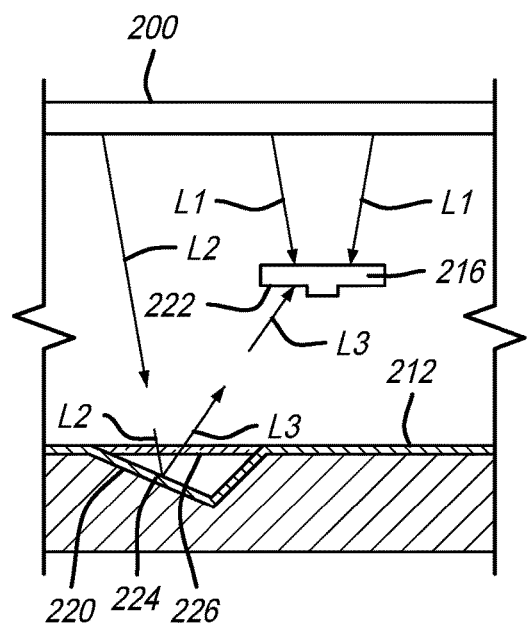
FIG. 17B is a schematic view showing an exemplary reflective surface covered with a transparent material from the UV sanitization system of FIG. 17.

FIGS. 17-17B show an example where a light assembly 200 is positioned under the mirror 208 in the lavatory and is positioned to sanitize surfaces on the sink 210, countertop 212, faucet 214, and soap dispenser 216, etc. The arrows in the figure represent the direction of the light rays. Light rays labeled L1 and L2 represent the light rays emitted from the light assembly 200. These rays are directed in a predetermined direction based on the lens member 202. Light rays L1 are targeted toward the direct surfaces to be sanitized 218. For example, see the arrows L1 that are directed toward the top of the faucet 214. Light rays L2 are targeted toward reflective surfaces 220 and light rays L3 are those reflected from a reflective surface 220 and directed to an indirect surface to be sanitized 222, for example, see the undersurface of the soap dispenser 216.

FIGS. 17-17B shows an exemplary reflective surface 220 on the countertop 212 that includes a UV reflective coating 224 thereon. The reflective surface 220 is angled differently than the countertop surface. As shown in FIGS. 17A and 17B, the angle of the reflective surface 220 is chosen to direct the light rays L3 to the underside of the soap dispenser 216, which is an indirect surface to be sanitized 222. As shown in FIG. 17B, the reflective surface 220 may include a transparent material 226 or coating thereon such that the reflective surface is "embedded" in the counter (wall, panel or other component that requires a reflective surface) so that it does not create a place for water to pool or dirt to collect. FIGS. 17A and 17B show the UV reflective coating on both the countertop surface and the angled reflective surface 220 (referred to herein as a "targeted reflective surface" 220). Some embodiments can include only targeted reflective surfaces 220 and other embodiments can include UV reflective coating 224 on many or all surfaces (referred to herein as "general reflective surfaces"), thus providing as much reflection as possible. Other embodiments, as shown in FIGS. 17A and 17B can include both.

FIG. 17 also shows exemplary targeted reflective surfaces 220 in the sink for reflecting the UV light onto the bottom of the faucet 214. These reflective surfaces are only exemplary and it should be appreciated that light assemblies 200 and targeted reflective surfaces 220 or general reflective surfaces may be located and positioned throughout the lavatory interior so as to strategically sanitize many surfaces and components. For example, FIGS. 3, 4 and 9, among others, show light modules 200 positioned throughout the lavatory interior (see also reflective surface 220 in FIG. 9). It will be appreciated that any component or area in the lavatory can be sanitized using UV light, for example, the door handles, the areas around the sink (sink basin 86) and countertop including the faucets, soap dispensers, and waste flaps (if present), and also certain areas associated with the toilet 112, toilet shroud 113, cover 118, the flush button 115, seat cover dispenser and the seat 117.

Figure 18:
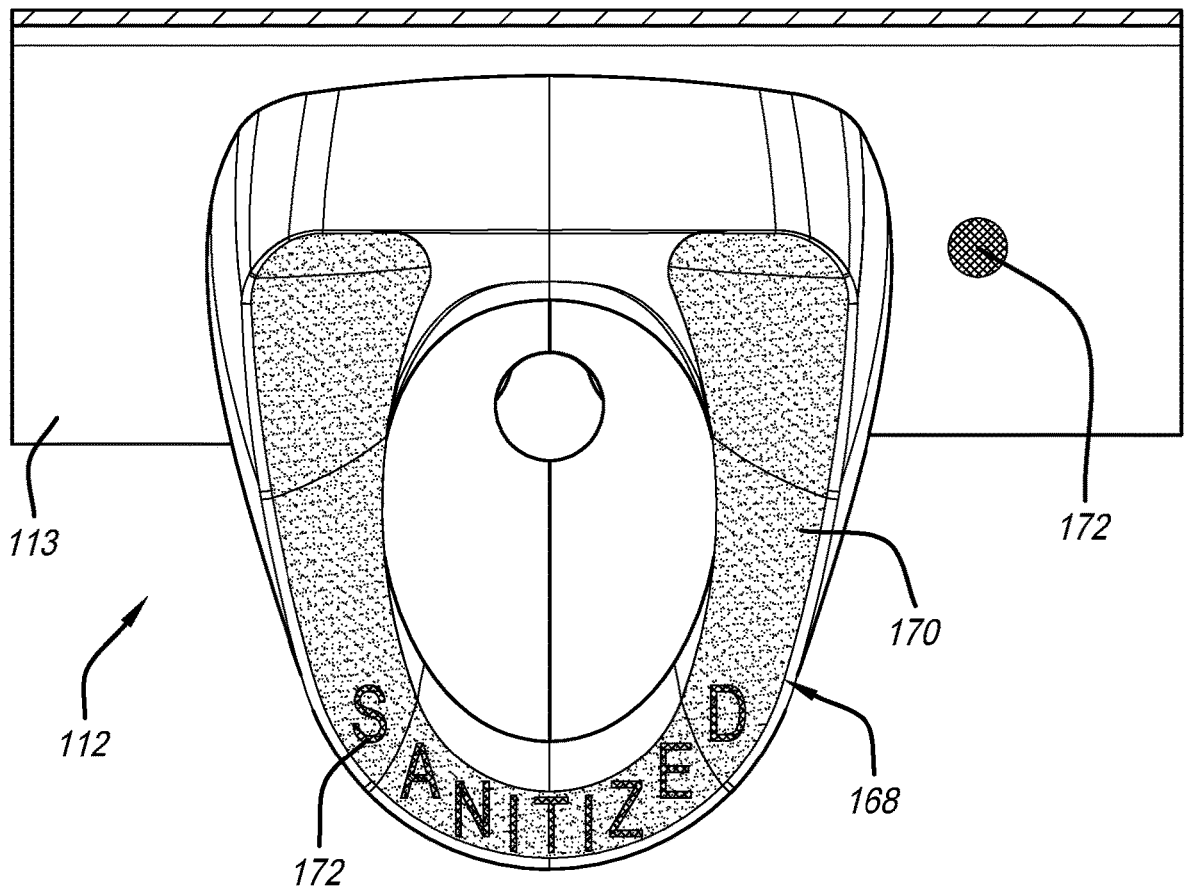
FIG. 18 is a top plan view of a toilet and shroud that include a coating with excitation additives.
Figure 19:
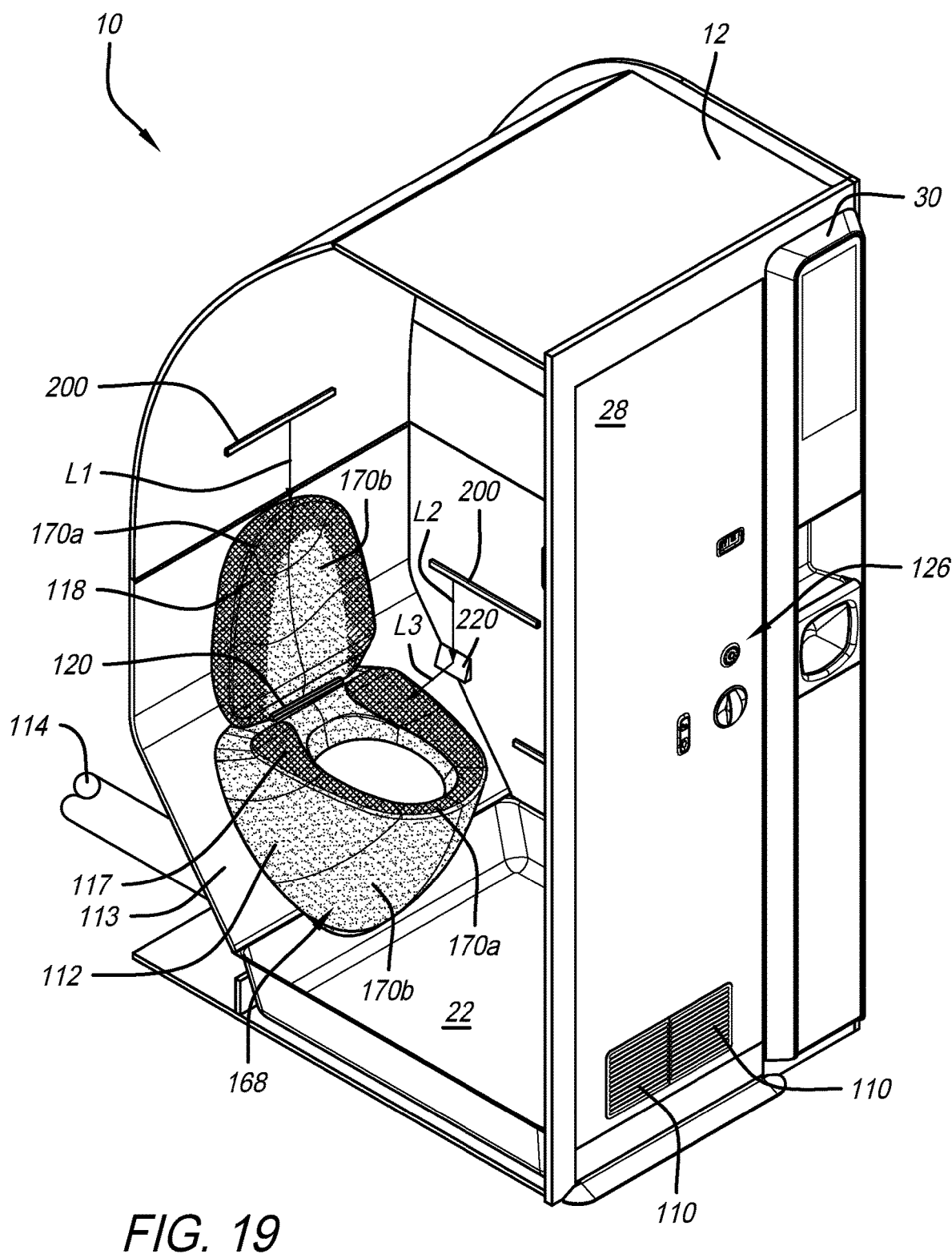
FIG. 19 is a perspective view of the lavatory monument assembly showing the toilet with two coatings thereon each with a different color excitation additive.

With reference to FIGS. 18-19, in a preferred embodiment, the lavatory monument assembly includes a visual indication system to do one or more of the following: provide a visual indication of "high priority areas" that require longer sanitization times using a UV light to sanitize surfaces: 2) provide a visual indication that antimicrobial additives are still present and active within a coating on surfaces on components in the lavatory; and/or 3) provide a visual indication that a surface has been recently sanitized.

The visual indication system is preferably included in coatings, films, panels, etc. (which may all be referred to herein as "visual indication coatings") that at least partially cover many or all of the surfaces of the components within the lavatory. The visual indication coatings include luminescing dyes or additives (also referred to herein as excitation additives) therein. In a preferred embodiment, the visual indication coatings also include antimicrobial additives, thus creating a visual indication coating that is also a sanitizing coating. The present invention includes the addition of additives or dyes in the sanitizing coatings or films that luminesce or illuminate when irradiated by light with a certain range of wavelengths (e.g., UV light, black light, etc.). The luminescence provides a visual indication of sanitization. The additives can be fluorescence and/or phosphorescence dyes that are defined by the wavelength of UV or laser energy used to create the desired response.

FIG. 18 shows a visual indication coating 168 that includes antimicrobial additives and first and second excitation additives that has been applied to or coated on the seat of the toilet 112. It will be appreciated that the toilet is only an example and visual indication coatings can be applied to the surface of any component within the lavatory. The first excitation additive is a fluorescent additive 170 and the second excitation additive is a phosphorescent additive 172. The fluorescent additive 170 can be used to show where the energy of the sanitizing UV light is directed. The stronger the excitation or fluorescing response as the UV light is directed toward a surface, the stronger the UV light illuminates and the better the level of sanitization is occurring. Bright or strong excitation equals strong sanitization, weak excitation equals weak sanitization. Therefore, in use, as the crew member directs the UV light closer to the toilet seat surface the fluorescing additive or dye will illuminate brighter. Also, as the crew member angles the UV light closer to the normal of the toilet seat surface the fluorescing additive or dye will illuminate brighter. This signals to the crew member to move the light closer and to angle it close to the normal of the surface.

In an embodiment where the lavatory includes the UV sanitization system discussed above, when the crew is in the process of positioning the light assemblies 200 and/or the reflective surfaces 220 and the UV coatings 224, the fluorescing additives can provide guidance as to the strength of the UV light reaching the direct and indirect surfaces to be sanitized.

Over time, the antimicrobial additive in the visual indication coating 168 may decay or breakdown. The fluorescent additives may decay or breakdown on a similar time scale or, if the antimicrobial additive and excitation additive are bonded to one another, the amount of excitation additive in the coating may decrease a the amount of antimicrobial additive decreases. As a result, the visual indication coating (and/or the fluorescent additives therein) may not illuminate as brightly during a cleaning than it previously did. This may indicate that the previous coating is not as effective at sanitizing and should be replaced. Scrubbing or washing surfaces over time may also cause a breakdown in the antimicrobial properties and/or excitation additives.

The phosphorescent additive 172 is included to provide a visual indication to both crew and passengers that the surface or visual indication coating 168 has been recently sanitized by UV light. As shown in FIG. 18, a predetermined pattern 174 can be included that provides the visual indication. FIG. 18 includes two predetermined patterns 18, the word "SANITIZED" on the toilet seat and a circular emblem on the shroud 113. Accordingly, each time the toilet seat is sanitized using UV light, the word SANITIZED will illuminate or luminesce, thus visually indicating to crew and passengers that the toilet seat should be clean. In an embodiment where the UV sanitizing system discussed herein is used, and the lavatory is sanitized after each use, the phosphorescent additive 172 will be illuminated each time a new passenger enters the lavatory. In a preferred embodiment, the predetermined pattern portion or symbol that shows that the lavatory was cleaned glows, illuminates or is excited for approximately 60 seconds after the UV sanitization system cleans the surfaces and then turns off. In this case, after the lavatory is automatically cleaned by the UV sanitization system, the passenger sees the symbol when they enter the lavatory (if immediately entering after cleaning), and by the time they are finished using the lavatory the symbol will be gone (the phosphorescence will no longer be excited). In another embodiment, where the system is not automated and the lavatory is UV sanitized prior to a flight, the phosphorescence or glow can last for several hours. As shown in FIG. 18, the entire visual indication coating includes the fluorescent additive 170 and only the predetermined pattern portion includes the phosphorescent additive 172. In other words, the predetermined pattern portion includes both the fluorescent additive 170 and phosphorescent additive 172 comingled.

In a preferred embodiment, the excitation additive or phosphorescent additive 172 can be added to the coating using an inkjet printer or the like (in another embodiment, the fluorescent additive 170 can also be added using inkjet printing). The coating base can be a clean thin film that can be put through an inkjet printer that includes the phosphorescent additive 172 therein. The printer prints the predetermined pattern or design on the film.

FIG. 19 shows an exemplary scenario where the toilet 112 includes first and second fluorescing additives 170a and 170b that each fluoresce or illuminate in a different color. It will be appreciated that the first and second fluorescing additives 170a and 170b may be included in the same coating or in separate coatings that are applied separately. In use, as the surfaces that are covered by the visual indication coating(s) 168 are exposed to UV light, first fluorescent additives 170*a* illuminate a first color and the second fluorescent additives 170*b* illuminate a second color. As shown in FIG. 19, the first fluorescent additives are on the high touch areas of the toilet seat and the rim of the toilet cover 118. Thus, the first color indicates to the crew member that the toilet seat and the rim of the toilet cover 118 require a longer sanitization time than the areas with the second color, which is a lower touch area.

The use of visual indication coatings in an aircraft lavatory is not a limitation on the present invention. The visual indication coatings can be used on any surface to be sanitized in an aircraft or vehicle or in any other scenario where a visual indication of the sanitization of a surface is desired. For example, visual indication coatings can be used in an aircraft on tray tables, seatbelts, door handles, armrests, gaspers, etc.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements: the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A vehicle lavatory monument assembly comprising:
    an enclosure that includes first, second, third and fourth walls that cooperate to define a lavatory interior, wherein an entry door is positioned on the second wall,
    a sink basin assembly positioned in the lavatory interior, wherein the sink basin assembly includes a sink basin that includes a back wall, a top wall, a bottom wall, a first side wall, and a second side wall that cooperate to defined a sink basin interior, wherein the top wall includes a top surface and a bottom surface, wherein the bottom surface partially defines the sink basin interior, and wherein the top surface is a counter, and
    a wipes panel positioned in the lavatory interior and that partially defines a wipes storage space, wherein the wipes panel includes a bottom edge that meets the top wall of the sink basin,
    wherein at least a first access opening is defined in the second wall, wherein a tower assembly is positioned over the first access opening, wherein the tower assembly includes a first door that is movable between an open and a closed position, wherein when the first door is in the open position, the lavatory interior is accessible from an exterior of the monument assembly, wherein the first door provides access to the wipes storage space within the lavatory interior.

2. The vehicle lavatory monument assembly of claim 1 wherein the sink basin assembly is positioned adjacent the third wall, wherein the top wall of the sink basin includes a front surface that angles inwardly from adjacent the entry door toward the third wall.

3. The vehicle lavatory monument assembly of claim 1 wherein the bottom wall, first side wall and second side wall of the sink basin include a handle portion on a front thereof.

4. The vehicle lavatory monument assembly of claim 3 wherein the handle portion is thicker than the bottom wall, first side wall and second side wall.

5. The vehicle lavatory monument assembly of claim 1 wherein a water dispenser is associated with the bottom surface of the top wall.

6. The vehicle lavatory monument assembly of claim 1 wherein the sink basin includes an ultraviolet light source configured to sanitize the sink basin.

7. The vehicle lavatory monument assembly of claim 1 wherein the top wall includes a curved portion that meets the bottom edge of the wipes panel.

8. The vehicle lavatory monument assembly of claim 1 further comprising a trash panel positioned in the lavatory interior, wherein the tower assembly includes a second door that is movable between an open position and a closed position, wherein the second door provides access to a trash receptacle space that is partially defined by the trash panel.

9. A vehicle lavatory monument assembly comprising:
an enclosure that includes first, second, third and fourth walls that cooperate to define a lavatory interior, wherein an entry door is positioned on the second wall,
a sink basin assembly positioned in the lavatory interior, wherein the sink basin assembly includes a sink basin that includes a back wall, a top wall, a bottom wall, a first side wall, and a second side wall that cooperate to defined a sink basin interior, wherein the top wall includes a top surface and a bottom surface, wherein the bottom surface partially defines the sink basin interior and the top surface is a counter, wherein the sink basin assembly is positioned adjacent the third wall, wherein the top wall of the sink basin includes a front surface that angles inwardly from adjacent the entry door toward the third wall, wherein the bottom wall, first side wall and second side wall of the sink basin include a handle portion on a front thereof, wherein the handle portion is thicker than the bottom wall, first side wall and second side wall, wherein water and soap dispensers are associated with the bottom surface of the top wall,
wherein at least a first access opening is defined in the second wall, wherein a tower assembly is positioned over the first access opening, wherein the tower assembly includes first and second doors that are each movable between an open and a closed position, wherein when the first and second doors are in the open position, the lavatory interior is accessible from an exterior of the monument assembly, wherein the first door provides access to a wipes storage space within the lavatory interior and the second door provides access to a trash receptacle space within the lavatory interior, wherein a wipes panel is positioned in the lavatory interior and partially defines the wipes space, and wherein the wipes panel includes a bottom edge that meets the top wall of the sink basin.

10. The vehicle lavatory monument assembly of claim 9, wherein a trash panel is positioned in the lavatory interior and partially defines the trash receptacle space.

11. The vehicle lavatory monument assembly of claim 10 wherein the sink basin includes an ultraviolet light source configured to sanitize the sink basin.

* * * * *